US010421990B2

(12) United States Patent
Lammertyn et al.

(10) Patent No.: US 10,421,990 B2
(45) Date of Patent: Sep. 24, 2019

(54) MONITORING DNA AMPLIFICATION

(71) Applicant: KATHOLIEKE UNIVERSITEIT LEUVEN, Leuven (BE)

(72) Inventors: Jeroen Lammertyn, Neerijse (BE); Karel Knez, Aalst (BE); Filip Delport, Temse (BE)

(73) Assignee: FOX BIOSYSTEMS NV, Temse (BE)

( * ) Notice: Subject to any disclaimer, the term of this patent is extended or adjusted under 35 U.S.C. 154(b) by 361 days.

(21) Appl. No.: 15/036,240

(22) PCT Filed: Nov. 12, 2014

(86) PCT No.: PCT/EP2014/074421
§ 371 (c)(1),
(2) Date: May 12, 2016

(87) PCT Pub. No.: WO2015/071338
PCT Pub. Date: May 21, 2015

(65) Prior Publication Data
US 2016/0298178 A1    Oct. 13, 2016

(30) Foreign Application Priority Data

Nov. 13, 2013  (GB) .................................. 1320071.2

(51) Int. Cl.
*C12Q 1/6825*  (2018.01)
*C12Q 1/6851*  (2018.01)
*C12Q 1/6862*  (2018.01)

(52) U.S. Cl.
CPC ......... *C12Q 1/6825* (2013.01); *C12Q 1/6851* (2013.01); *C12Q 1/6862* (2013.01)

(58) Field of Classification Search
None
See application file for complete search history.

(56) References Cited

U.S. PATENT DOCUMENTS 6,617,137 B2 * 9/2003 Dean .................... C12Q 1/6806
435/91.1

FOREIGN PATENT DOCUMENTS

EP    1947197 A1    7/2008
WO    2009014830 A1    1/2009

OTHER PUBLICATIONS

Knez et al. Analytical Chemistry 2013; 85: 1734-1742 (Year: 2013).*
Janssen et al. Nanotechnology 2012; 23: 235503 (Year: 2012).*
Murray et al., "Modeling the Impact of Global Tuberculosis Control Strategies," The National Academy of Sciences, Nov. 1998, pp. 13881-13886, vol. 95, Harvard School of Public Health, Cambridge.
Wittwer et al., "Real-Time Multiplex PCR Assays," Methods, 2001, pp. 430-442, vol. 25, University of Utah School of Medicine, Salt Lake City.
Mackay et al., "Survey and Summary Real-Time PCR in Virology," Nucleic Acids Research, Jan. 14, 2002, pp. 1292-1305, vol. 30, No. 6, Oxford University Press.
Espy et al., "Real-Time PCR in Clinical Microbiology: Applications for Routine Laboratory Testing," Clinical Microbiology Reviews, Jan. 2006, pp. 165-256, vol. 19, No. 1, American Society for Microbiology, Rochester.
Malanoski et al., "Automated Identification of Multiple Micro-Organisms from Resequencing DNA Microarrays," Nucleic Acids Research, Jul. 19, 2006, pp. 5300-5311, vol. 34, No. 18, Oxford University Press, Washington DC.
Li et al., "s-RT-MELT for Rapid Mutation Scanning Using Enzymatic Selection and Real-Time DNA-Melting: New Potential for Multiplex Genetic Analysis," May 2, 2007, pp. 1-11, vol. 35, No. 12.
Fiche et al., "Point Mutation Detection by Surface Plasmon Resonance Imaging Coupled with a Tempeture Scan Method in a Model System," Analytical Chemistry, 2008, pp. 1049-1057, vol. 80.
Lodeiro et al., "Light and Colour as Analytical Detection Tools: A Journey into the Periodic Table Using Polyamines to Bio-Inspired Systems as Chemosensors," Chemical Society Reviews, 2010, pp. 2948-2976, vol. 39.
Pollet et al., "Real-Time Monitoring of Solid-Phase PCR Using Fiber-Optic SPR," Small, 2011, pp. 1003-1006, vol. 7, No. 8.
Gervais et al., "Microfluidic Chips for Point-of-Care Immunodiagnostics," Advanced Healthcare Materials, 2011, pp. H151-H176, vol. 23.
Cornett et al., "Molecular Logic gates for DNA Analysis: Detention of Rifampin Resistance in M.Tuberculosis DNA," Angrew Chem Int Ed Engl., Sep. 3, 2012, pp. 9075-9077, vol. 51, No. 36.
Delport et al., "Real-Time Monitoring of DNA Hybridization and Melting Processes Using a Fiber Optic Sensor," Nanotechnology, Jan. 17, 2012, pp. 1-7, vol. 23.
Knez et al., "Fiber-Optic High Resolution Genetic Screening using Gold-Label Gene Probes," Small, 2012, pp. 1-5, vol. 8.
Liao et al., "Combination of Fluorescence Color and Melting Temperature as a Two-Dimensional Label for Homogeneous Multiplex PCR Detection," Nucleic Acids Research, Jan. 18, 2013, pp. 1-11, vol. 41 No. 7, Oxford University Press.
International Search Report from corresponding PCT Application No. PCT/EP2014/074421, dated Feb. 13, 2015.
Knez et al., "Sperical Nucleic Acid Enhanced FO-SPR DNA Melting for Detection of Mutations in Legionella Pneumophila," Analytical Chemistry, Jan. 2013, pp. 1734-1742, vol. 85.

(Continued)

*Primary Examiner* — Angela M. Bertagna
(74) *Attorney, Agent, or Firm* — Workman Nydegger

(57) ABSTRACT

A method and kits are provided for nucleic acid quantification and discrimination using surface plasmon resonance (SPR). The method provided is able to significantly enhance the detection limit and multiplex the discrimination assay using the melting properties of the target DNA on top of standard PCR reaction. By using the heating and cooling cycles of the polymerase chain reaction (PCR) or Ligation chain reaction (LCR), DNA is melted and hybridized onto the SPR sensor surface together with a nanoparticle label. Thus, during every cycle of DNA amplification, the quantity and type of target DNA can be monitored.

18 Claims, 12 Drawing Sheets
Specification includes a Sequence Listing.

(56) References Cited

OTHER PUBLICATIONS

Great Britain Search Report from corresponding Great Britain Application No. GB1320071.2, dated Jul. 28, 2014.
International Preliminary Report on Patentability from corresponding PCT Application No. PCT/EP2014/074421, dated May 26, 2016.
European Office Action from EP Application No. 14803071.1, dated Mar. 7, 2017.
Examination Report from European Patent Office from EP Application No. EP 14803071, dated Mar. 9, 2018.
European Office Communication from EP Application No. EP 14803071.1, dated Sep. 3, 2018.
European Office Communication from EP Application No. 14803071.1, dated Apr. 18, 2019.

* cited by examiner

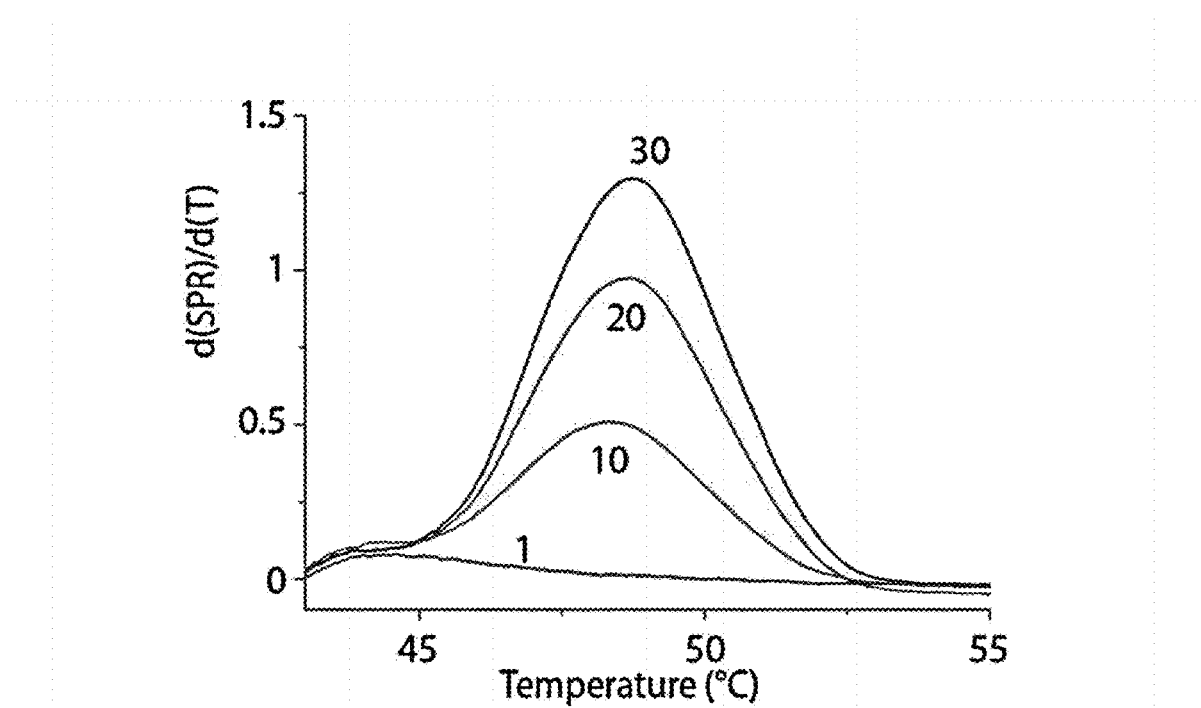
Figure 7
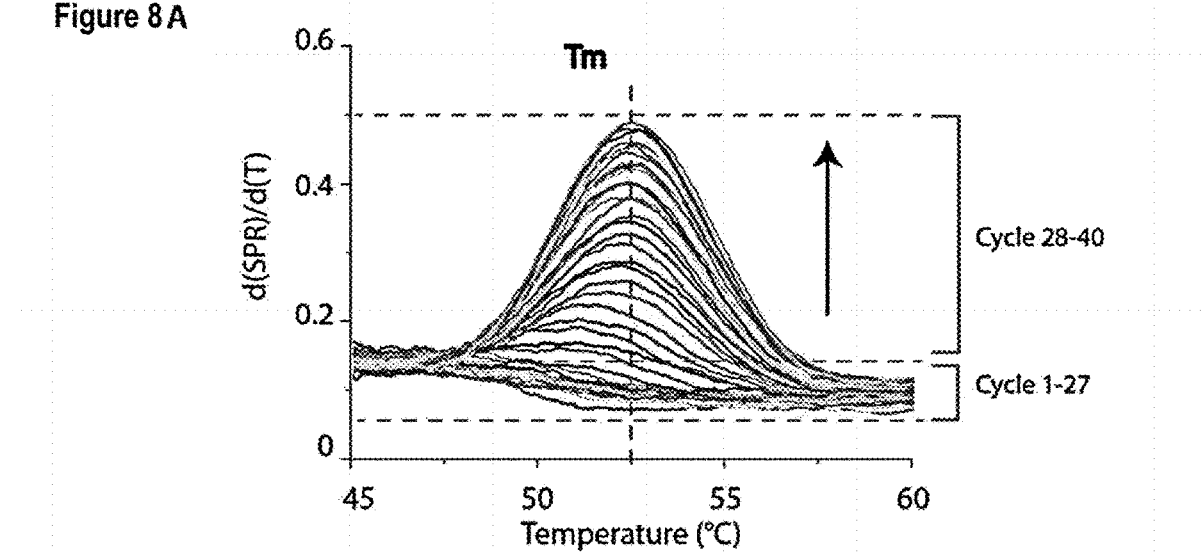

SEQUENCE LISTING

<160> NUMBER OF SEQ ID NOS: 29

<210> SEQ ID NO 1
<211> LENGTH: 30
<212> TYPE: DNA
<213> ORGANISM: Bacillus anthracis

<400> SEQUENCE: 1
atccttatca atatttaaca ataatccctc                30

<210> SEQ ID NO 2
<211> LENGTH: 30
<212> TYPE: DNA
<213> ORGANISM: Bacillus anthracis

<400> SEQUENCE: 2
atccttatca atgtttaaca ataatccctc                30

<210> SEQ ID NO 3
<211> LENGTH: 15
<212> TYPE: DNA
<213> ORGANISM: Bacillus anthracis

```
<400> SEQUENCE: 3
aatattgata aggat                                                    15

<210> SEQ ID NO 4
<211> LENGTH: 15
<212> TYPE: DNA
<213> ORGANISM: Bacillus anthracis

<400> SEQUENCE: 4
gagggattat tgtta                                                    15

<210> SEQ ID NO 5
<211> LENGTH: 15
<212> TYPE: DNA
<213> ORGANISM: Bacillus anthracis

<400> SEQUENCE: 5
taacaataat ccctc                                                    15

<210> SEQ ID NO 6
<211> LENGTH: 15
<212> TYPE: DNA
<213> ORGANISM: Bacillus anthracis

<400> SEQUENCE: 6
atccttatca atatt                                                    15

<210> SEQ ID NO 7
<211> LENGTH: 15
<212> TYPE: DNA
<213> ORGANISM: Bacillus anthracis

<400> SEQUENCE: 7
aacattgata aggat                                                    15

<210> SEQ ID NO 8
<211> LENGTH: 15
<212> TYPE: DNA
<213> ORGANISM: Bacillus anthracis

<400> SEQUENCE: 8
atccttatca atgtt                                                    15

<210> SEQ ID NO 9
<211> LENGTH: 16
<212> TYPE: DNA
<213> ORGANISM: Bacillus anthracis

<400> SEQUENCE: 9
taacaataat ccctca                                                   16

<210> SEQ ID NO 10
<211> LENGTH: 15
<212> TYPE: DNA
<213> ORGANISM: Bacillus anthracis

<400> SEQUENCE: 10
atccttatca atatt                                                    15

<210> SEQ ID NO 11
<211> LENGTH: 76
<212> TYPE: DNA
```

<213> ORGANISM: Mycobacterium bovis

<400> SEQUENCE: 11
gcagaagcgc aacactcttg gagtggccta caacggcgct ctccgcggcg cgggcgtacc    60
ggatatctta gctggt    76

<210> SEQ ID NO 12
<211> LENGTH: 76
<212> TYPE: DNA
<213> ORGANISM: Mycobacterium bovis

<400> SEQUENCE: 12
gcagaagcgc aacactcttt gagtggccta caacggcgct ctccgcggcg cgggcgtacc    60
ggatatctta gctggt    76

<210> SEQ ID NO 13
<211> LENGTH: 76
<212> TYPE: DNA
<213> ORGANISM: Mycobacterium bovis

<400> SEQUENCE: 13
gcagaagcgc aacactcttt gagcgtccta caacggcgct ctccgcggcg cgggcgtacc    60
ggatatctta gctggt    76

<210> SEQ ID NO 14
<211> LENGTH: 53
<212> TYPE: DNA
<213> ORGANISM: Mycobacterium avium subspecies paratuberculosis

<400> SEQUENCE: 14
tggtcgtctg ctgggttgat ctggacaatg acggttacgg aggtggttgt ggc    53

<210> SEQ ID NO 15
<211> LENGTH: 53
<212> TYPE: DNA
<213> ORGANISM: Mycobacterium avium subspecies paratuberculosis

<400> SEQUENCE: 15
tggtcgtctg ctgggttgat atggacaatg acggttacgg aggtggttgt ggc    53

<210> SEQ ID NO 16
<211> LENGTH: 53
<212> TYPE: DNA
<213> ORGANISM: Mycobacterium avium subspecies paratuberculosis

<400> SEQUENCE: 16
tggtcgtctg ctgggttgat attaacaatg acggttacgg aggtggttgt ggc    53

<210> SEQ ID NO 17
<211> LENGTH: 19
<212> TYPE: DNA
<213> ORGANISM: Mycobacterium bovis

<400> SEQUENCE: 17
gcagaagcgc aacactctt    19

<210> SEQ ID NO 18
<211> LENGTH: 22
<212> TYPE: DNA
<213> ORGANISM: Mycobacterium bovis

<400> SEQUENCE: 18

```
accagctaag atatccggta cg                                            22

<210> SEQ ID NO 19
<211> LENGTH: 19
<212> TYPE: DNA
<213> ORGANISM: Mycobacterium avium subspecies paratuberculosis

<400> SEQUENCE: 19
tggtcgtctg ctgggttga                                                19

<210> SEQ ID NO 20
<211> LENGTH: 20
<212> TYPE: DNA
<213> ORGANISM: Mycobacterium avium subspecies paratuberculosis

<400> SEQUENCE: 20
gccacaacca cctccgtaac                                               20

<210> SEQ ID NO 21
<211> LENGTH: 48
<212> TYPE: DNA
<213> ORGANISM: Mycobacterium bovis

<400> SEQUENCE: 21
cgccgttgta ggccactcca agagtgttgc gcttctgctt tttttttt                48

<210> SEQ ID NO 22
<211> LENGTH: 48
<212> TYPE: DNA
<213> ORGANISM: Mycobacterium bovis

<400> SEQUENCE: 22
tttttttttt accagctaag atatccggta cgcccgcgcc gcggagag                48

<210> SEQ ID NO 23
<211> LENGTH: 45
<212> TYPE: DNA
<213> ORGANISM: Mycobacterium avium subspecies paratuberculosis

<400> SEQUENCE: 23
tgtccagatc aacccagcag acgaccattt tttttttttt ttttt                   45

<210> SEQ ID NO 24
<211> LENGTH: 44
<212> TYPE: DNA
<213> ORGANISM: Mycobacterium avium subspecies paratuberculosis

<400> SEQUENCE: 24
tttttttttt ttttttttgc cacaaccacc tccgtaaccg tcat                    44

<210> SEQ ID NO 25
<211> LENGTH: 109
<212> TYPE: DNA
<213> ORGANISM: Apium graveolens

<400> SEQUENCE: 25
cccgtacgag atatattttt gtctggtttg agatatatat tacatgctga gtcacgatga   60
gcgtgtactg agtcagtgtt atgtttggat tacggtgtga tgagtcagc              109

<210> SEQ ID NO 26
<211> LENGTH: 26
<212> TYPE: DNA
```

```
<213> ORGANISM: Apium graveolens

<400> SEQUENCE: 26
cccgtacgag atatattttt gtctgg                                          26

<210> SEQ ID NO 27
<211> LENGTH: 23
<212> TYPE: DNA
<213> ORGANISM: Apium graveolens

<400> SEQUENCE: 27
gctgactcat cacaccgtaa tcc                                             23

<210> SEQ ID NO 28
<211> LENGTH: 65
<212> TYPE: DNA
<213> ORGANISM: Apium graveolens

<400> SEQUENCE: 28
gtgactcagc atgtaatata tatctcaaac cagacaaaaa tatatctcgt acgggttttt     60
ttttt                                                                 65

<210> SEQ ID NO 29
<211> LENGTH: 64
<212> TYPE: DNA
<213> ORGANISM: Apium graveolens

<400> SEQUENCE: 29
tttttttttt gctgactcat cacaccgtaa tccaaacata acactgactc agtacacgct    60
catc                                                                 64
```

MONITORING DNA AMPLIFICATION

FIELD OF THE INVENTION

The invention relates to real-time detection, identification, and quantification of nucleic acids targets using a mass sensitive biosensor, such as a fibre optic surface plasmon resonance (FO-SPR) device, in combination with nucleic acid amplification reactions such as polymerase chain reaction (PCR) and ligation chain reaction (LCR).

REFERENCE TO SEQUENCE LISTING SUBMITTED VIA EFS-WEB

This application includes an electronically submitted sequence listing in .txt format. The .txt file contains a sequence listing entitled "19893-14-Sequence_Listing.txt" created on May 6, 2016 and is 6 bytes in size. The sequence listing contained in this .txt file is part of the specification and is hereby incorporated by reference herein in its entirety.

BACKGROUND OF THE INVENTION

The detection, identification, and quantification of nucleic acids are fundamental to many diagnostic tests for infection, disease, contaminants, and/or allergens. In these tests, the diagnosis and sometimes prognosis of a pathological condition is based on the presence of minute quantities of nucleic acids from a microorganism or a cell. Identification of multiple pathogens and their phenotypes as well as one or more specific gene mutations and quantification of nucleic acids, particularly from microorganisms, are also important steps in establishing the cause of an infection [Cornett et al., *Angew Chem Int Ed Engl*, 2012, 51, 9075-9077; Murray & Salomon, *Proc. Natl. Acad. Sci USA*, 1998, 95, 13881-13886. Malanoski et al. *Nucleic acids res.*, 2006, 34, 5300-5311]. Similarly, the identification and quantification of single nucleotide polymorphisms (SNPs) in genes like BRCA, p53, and KRAS provides information about cancer and other diseases.

While scientific research contributes to the breadth of diagnostic tests, speed and convenience play an increasingly prominent role in the testing methods. Multiplex assays, in which multiple analytes are measured in a single run/cycle of the assay, and point of care (POC) testing, in which tests are performed at or near the site of patient care, are expected to deliver fast and affirmative results [Gervais et al., *Adv Mater*, 2011, 23, H151-H176]. For nucleic acid analysis, techniques such as DNA melting analysis using high resolution instrumentation and specialized fluorescent DNA-binding dyes are used to determine the presence and identity of different nucleic acids in the same solution. Another technique based on qPCR powerfully combines sensitive nucleic acid detection in real-time with multiplexing capacity [Espy et al., *Clin Microbiol Rev*, 2006, 19, 165-256]. However, these techniques require the use of multiple fluorescent dyes to monitor the amplification of target nucleic acids in real-time [Lodeiro et al., *Chem Soc Rev*, 2010, 39, 2948-2976]. Because resonance energy transfer occurs between the dyes, the sensitivity of these reactions is hampered, and most qPCR assays can simultaneously detect only 2-3 targets [Wittwer et al., *Methods*, 2001, 25, 430-442]. Conventional PCR performed without dyes could support many more targets, as evidenced by experiments in which the characteristic melting temperature ($T_m$) of PCR amplicons were used as a secondary label in qPCR, leading to identification of 50 different DNA sequences in one sample [Mackay et al. *Nucleic acids res.*, 2002, 30, 1292-1305; Liao et al., *Nucleic acids res.*, 2013, 41, e76]. Moreover, although multiplex DNA detection based on the melting temperature ($T_m$) analysis has been applied many times in PCR assays, the melting analysis is always applied post PCR, and does not allow for monitoring of specific targets during the PCR reaction [Li et al. *Nucleic acids res.*, 2007, 35, e84]. As a result, the melting analysis can be used to detect the presence of DNA targets, but cannot be used to quantitate DNA. These limitations make the technology better-suited as a screening tool for the presence of mutations, but there remains a need in the art for techniques which enable rapid, sensitive, and accurate identification and quantification of nucleic acid targets.

To monitor DNA amplification during PCR reactions, DNA melting can be followed in real-time using surface plasmon resonance (SPR) devices. An SPR imaging device was used to discriminate between SNPs in short target sequences, [Fiche et al., *Analytical Chemistry*, 2008, 80, 1049-1057] while hybridization of Au NPs to the surface of the SPR devices improved resolution so that SNPs were discriminated in longer targets (PCR amplicons) [Knez et al., *Small*, 2012, 8, 868-872]. Herein a PCR reaction is performed with one primer pair to detect different mutations within the same target nucleic acid. After completion of the amplification reaction the presence of different mutated forms is detected in a separate sensor device by determining the melting temperature of the different mutants.

For the latter studies, a fibre optic SPR (FO-SPR) device was used as a "dip probe" to test different solutions. The FO-SPR device was used primarily for monitoring solid phase PCR amplification reactions, although efficiency was limited [Pollet et al. *Small*, 2011. 7, 1003-1006] In this method the solid phase PCR reaction is performed using one primer which is attached to the sensor and one primer which is attached to a gold particle. The probes on the surface are extended during PCR and determination of the melting point is thus dictated by the behaviour of the entire amplicon and not just by primer template hybridisation.

Multiplex PCR reactions would only be possible by using multiple fibres (i.e., an individually functionalized fibre for each amplification reaction).

Delport et al. (2012) *Nanotechnology* 23, 065503, measures the melting point of a double stranded DNA wherein one strand is attached to the surface of a fibre optic sensor and the second strand is attached to a silica nanoparticle.

SUMMARY OF THE INVENTION

Described herein are methods for detection, identification, and quantification of nucleic acid targets using improved FO-SPR-based technology. The methods are used for real-time analysis of single or multiple nucleic acid targets, and in contrast to earlier studies, combine solution-based amplification reactions with surface-based detection methods.

Solution based amplification means that the primers used for amplification are not coupled to the sensor surface in the reaction chamber.

The methods make use of melting temperature analysis conducted during nucleic acid amplification reactions, which are monitored as target nucleic acids bind to or melt from the surface of the FO-SPR device during amplification. Amplification reactions such as PCR and LCR are integrated with a FO-SPR device. The amplification reaction takes place in the same reaction chamber in the buffer wherein also the sensor probe resides.

The present invention relates to a method for real-time detection of two or more target nucleic acids in a solution, comprising: (a) obtaining a fibre optic (FO) sensor functionalized with a first set of nucleic acid probes; (b) obtaining metal nanoparticles each functionalized with a second set of nucleic acid probes; (c) combining the sample with nucleic acid primers in solution whose sequences are complementary to the two or more target nucleic acids; (d) conducting nucleic acid amplification reactions comprising amplification cycles to amplify the two or more target nucleic acids in the presence of the FO sensor, metal nanoparticles, and nucleic acid primers; and (e) measuring a refractive index at the FO sensor during the nucleic acid amplification reactions; wherein measurable shifts in the refractive index at specific temperatures reached during the nucleic acid amplification reactions indicates the presence of each of the two or more target nucleic acids.

An aspect of the invention relates to methods for real-time detection of a target nucleic acid in a sample, comprising the steps of:
a) providing a reaction chamber comprising:
  a mass sensitive sensor, wherein the sensor is functionalized with a first nucleic acid probe hybridizing to said target nucleic acid, and
  metal nanoparticles functionalized with a second nucleic acid probe hybridizing to said target nucleic acid, wherein said first and second probes bind to different regions of the target nucleic acid such that both first and second probes can hybridize simultaneously to the target nucleic acid,
b) adding a sample to the reaction chamber and performing, with the sensor being present within the reaction chamber, a nucleic acid amplification of the target nucleic acid using non-immobilized probes complementary to the target nucleic DNA, wherein during the annealing step of the amplification method amplified target nucleic acid forms a complex with the first probe on the sensor and the second probe with the metal particle,
c) determining during the denaturation step of the nucleic acid amplification reaction the presence of target nucleic acid at the sensor by measuring at the melting temperature of the complex formed in step b, the release of target nucleic acid from the sensor.

Typically, these methods are multiplex assays for the detection of a plurality of different target nucleic acids, wherein for each of the different target nucleic acids, a specific set of first probe on the sensor and second probe on the metal particle are provided, and wherein non-immobilised amplification primers are provided to amplify all target nucleic acids, such that for each of the complexes of different nucleic acid target and its corresponding first and second probe a different melting temperatures is obtained, and wherein by measuring at the melting temperature of each of the different nucleic acid target complexes, the presence of each of the different target nucleic acids on the sensor is determined.

In these multiplex assays the difference in melting temperature between each of the different complexes is at least 0.3 degrees, at least 0.4 degrees, at least 0.6 degrees at least 0.9, at least 1.2 degrees or even at least 1.5° C.

In specific embodiments of the above multiplex assays the first probes for the different target nucleic acids are immobilised on the same sensor surface.

In specific embodiments of the assays of the present invention the non-immobilized primers for amplification are present in the reaction chamber prior to the addition of the sample.

Typically, the metal particles in the assays of the present invention are gold particles.

In embodiments of the methods of the present invention, the mass sensitive sensor is an optic sensor, such as a fibre optic sensor In some embodiments, the nucleic acid amplification reactions are selected from PCR and LCR.

In some embodiments, the specific temperatures at which measurable shifts in refractive index occur correspond with melting temperatures at which each target nucleic acid separates from its complementary nucleic acid probes.

The measurable shifts in the refractive index signals may be compared with a calibration curve indicating expected melting temperatures for each target nucleic acid.

In some embodiments, quantities of each target nucleic acid are determined in real-time by counting amplification cycles needed to produce the measurable shift in refractive index.

Amplification cycles may be compared with a reference curve indicating nucleic acid concentration as a function of amplification cycles.

In certain embodiments, the nucleic acid amplification reactions comprise at least 5 amplification cycles each comprising a denaturation step, an annealing step, and an extension step. For example, the nucleic acid amplification reactions may comprise at most 65 amplification cycles.

In some embodiments, the amplification cycles comprise at least one cycle in which melting rates are in a range between 0.1° C./s-1.5° C./s. In some embodiments, the amplification cycles comprise at most 50 cycles in which ramp speeds are in a range between 1° C./s to 8° C./s. In certain embodiments, the amplification cycles comprise at most 50 cycles in which ramp speeds are between 1.0° C./s-8.0° C./s and, optionally, melting rates in at least one cycle are in a range between 0.1° C./s-1.5° C./s.

The amplification reactions may comprise a denaturation step of less than 5 seconds in duration. In some embodiments, the amplification cycles comprise an elongation step of at least 10 seconds in duration. The amplification cycles may comprise an elongation step of no more than 60 seconds in duration.

In some embodiments, the refractive index at the FO sensor is continuously measured during the amplification cycles of the DNA amplification reaction. The refractive index at the FO-SPR sensor may be measured during at least one of a denaturation phase, an annealing phase, or an extension phase of at least one amplification cycle.

In some embodiments, the solution contains at least two target nucleic acids. For example, the solution may contain 2, 3, 4, 5, 6, 7, 8, 9, or 10 target nucleic acids.

In certain embodiments, the target nucleic acids are sequences that differ by at least one nucleic acid. Target nucleic acids may be DNA and/or RNA.

In some embodiments, the first set of nucleic acid probes comprises oligonucleotides whose sequences are complementary to a first strand of each target nucleic acid. In certain embodiments, the second set of nucleic acid probes comprises oligonucleotides whose sequences are complementary to a second strand of each target nucleic acid. In certain embodiments, the nucleic acid primers comprises oligonucleotides whose sequences are complementary to a first strand of each target nucleic acid and oligonucleotides whose sequences are complementary to a second strand of each target nucleic acid.

A further aspect of the present disclosure relates to a method for real-time detection of two or more target nucleic acids in a solution, comprising: (a) obtaining a fibre optic (FO) sensor functionalized with a first set of nucleic acid probes; (b) obtaining metal nanoparticles each functionalized with a second set of nucleic acid probes; (c) combining the sample with nucleic acid primers in solution whose sequences are complementary to the two or more target nucleic acids; (d) conducting PCR comprising amplification cycles to amplify the two or more target nucleic acids in the presence of the FO sensor, metal nanoparticles, and nucleic acid primers, wherein the PCR is held for at most 60 seconds at a temperature during an elongation step and held less than 1 second at a temperature during a denaturation step; and (e) measuring a refractive index at the FO sensor during the DNA amplification reactions; wherein measurable shifts in the refractive index at specific temperatures reached during PCR indicates the presence of each of the two or more target nucleic acids.

Another aspect of the present disclosure relates to a method for real-time detection and/or quantification of two or more target nucleic acids in a solution comprising: (a) obtaining a fibre optic (FO) sensor functionalized with a first set of nucleic acid probes; (b) obtaining metal nanoparticles each functionalized with a second set of nucleic acid probes; (c) combining the sample with nucleic acid primers in solution whose sequences are complementary to the two or more target nucleic acids; (d) conducting LCR comprising amplification cycles to amplify the two or more target nucleic acids in the presence of the FO sensor, metal nanoparticles, and nucleic acid primers, wherein the amplification cycle is held at a probe hybridization temperature for at most 3 minutes, a ligation temperature for at most 3 minutes, and a denaturing temperature for at most 5 seconds; and (e) measuring a refractive index at the FO sensor during the LCR; wherein measurable shifts in the refractive index at specific temperatures reached during the LCR indicates the presence of each of the two or more target nucleic acids.

A further aspect of the present invention relates to kit of reagents for determining a target nucleic acid in a sample comprising:

a mass sensitive sensor probe functionalized with a first nucleic acid probe hybridizing to said target, and metal nanoparticles functionalized with a second nucleic acid probe hybridizing to said target nucleic acid, wherein the first and second probes bind to different regions of the target nucleic acid such that both first and second probes can hybridize simultaneously to the target nucleic acid, characterized in the further presence of non-immobilized amplification primers for amplifying said target DNA.

This kit can be a kit for determining in a multiplex assay a plurality of different target nucleic acids, comprising for each of the different target nucleic acids, a first nucleic acid probe on said sensor and a second nucleic acid on a metal nanoparticle, and comprising non-immobilised amplification primers to amplify all target nucleic acids, whereby the first and second probes are chosen such that the melting temperature for each complex of different target nucleic acid with first and second probe differs from each other.

In embodiments of these kits the probes in the kit are designed such that the difference in melting temperature between each of the different complexes is at least 0.3 degrees, preferably at least 1.5° C.

In embodiments of these kits the sensor is a fibre optic sensor.

In embodiments of these kits the sensor is a fibre optic sensor and the different first probes are immobilised on the same optic fibre.

In embodiments of these kits the metal nanoparticles are gold particles.

Further disclosed in this application are devices for the detection of nucleic acids comprising:

a controllable heating device for performing a non-isothermal amplification of a target nucleic acid in a sample, and a mass sensitive sensoring device for detecting the presence of a nucleic acid in a sample, wherein the heating device and the sensing device are positioned such that detection of the nucleic acid by the sensor can be performed during the nucleic acid amplification.

In these devices, the sensor is typically an optic sensor, more typically a fibre optic sensor.

BRIEF DESCRIPTION OF DRAWINGS

FIG. 7 shows the melting signal of each cycle is obtained by plotting the derivative of the FO-SPR signal and thermocouple signal during the melting phase as a function of temperature. The cycle number is shown in the graphs.

FIGS. 8A-8C shows A) FO-SPR LCR reaction results for one concentration of target DNA (100 fM). The results are an overlay of the derived melting signal obtained from 40 thermal cycles. Starting from cycle 27 the melting peak height gradually increases (indicated by the arrow). B) The increase in melting peak signal for different target concentrations (100 nm, 10 nm, 1 nm, 100 pM, 10 pM, 1 pM, 100 fM and NTC, each with a repetition) is represented as sigmoidal second order fit of the corresponding points. (The concentration for each pair is indicated by a number, which number is also in the graph).

The horizontal line indicates the cycle threshold (Ct) used to derive a calibration curve. C) The derived calibration curve of Ct values, with a linear range spanning 7 orders of magnitude for DNA concentrations. The line is a logarithmic fit of the Ct values for each measured concentration ($R^2$=0.99). Variability is expressed as standard deviation (n=2).

Figure 9:
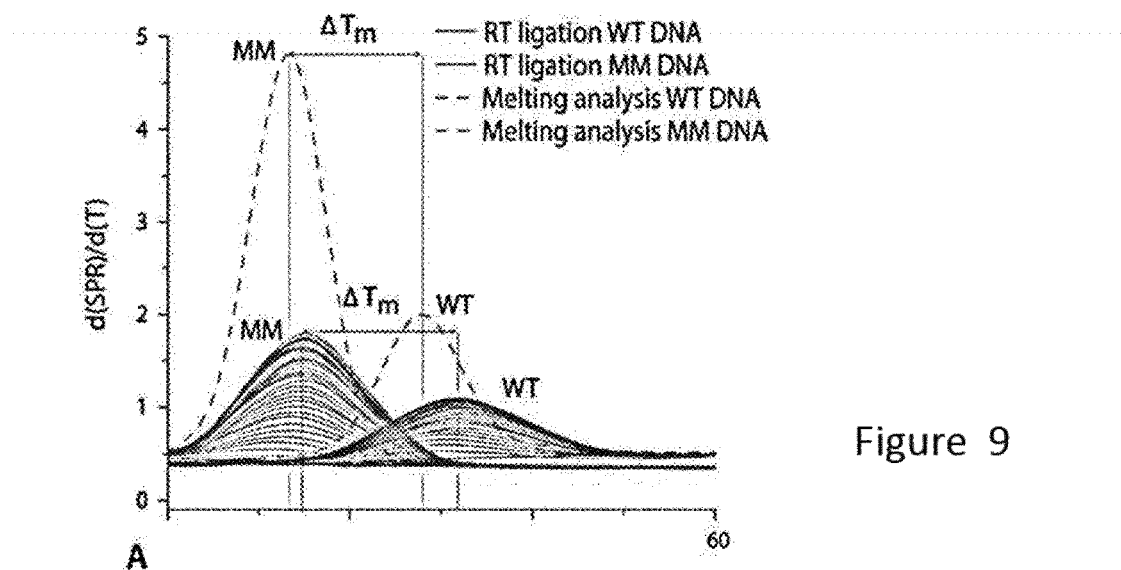

FIG. 9 shows obtained signals for the FO-SPR LCR assay using WT (wild-type) and MM (mutant) target DNA (target [C]=10 nM). The mutant clearly has a higher yield but a lower melting point.

Figure 10:
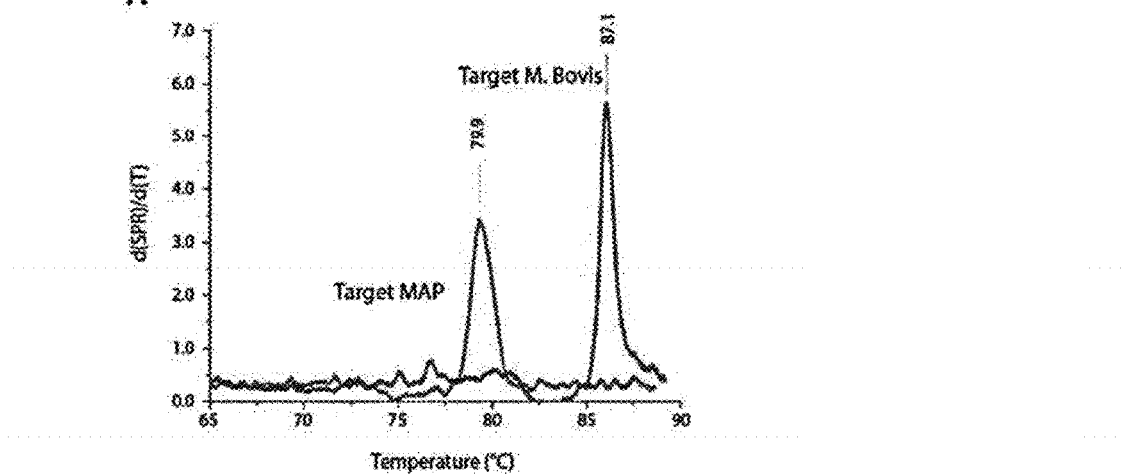
Figure 10:
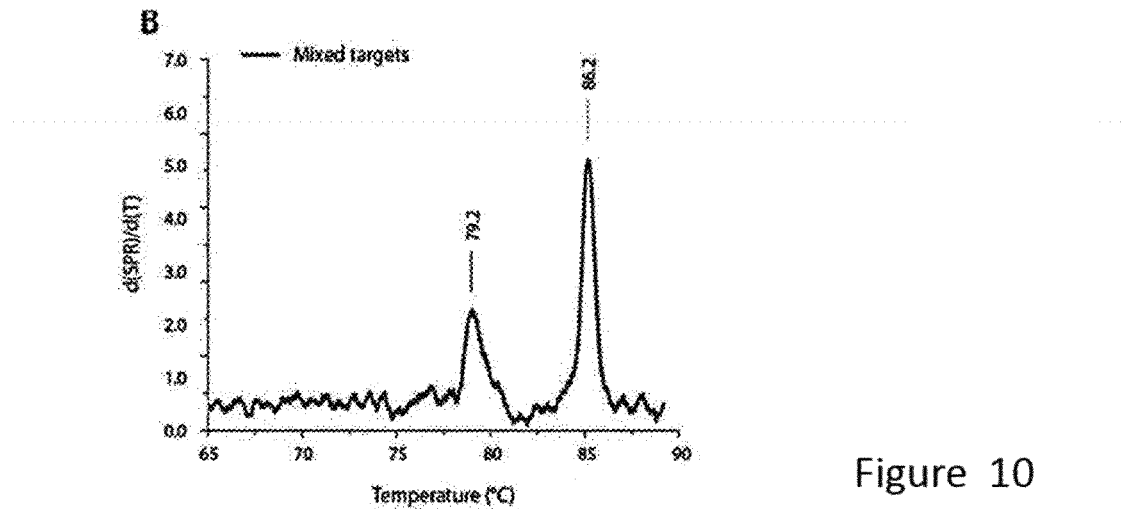

FIG. 10 shows A) Individual and B) Multiplex FO-SPR melting analysis for the MAP (*Mycobacterium avium* subspecies *paratuberculosis*) and *Mycobacterium bovis* target sequences.

Figure 11:
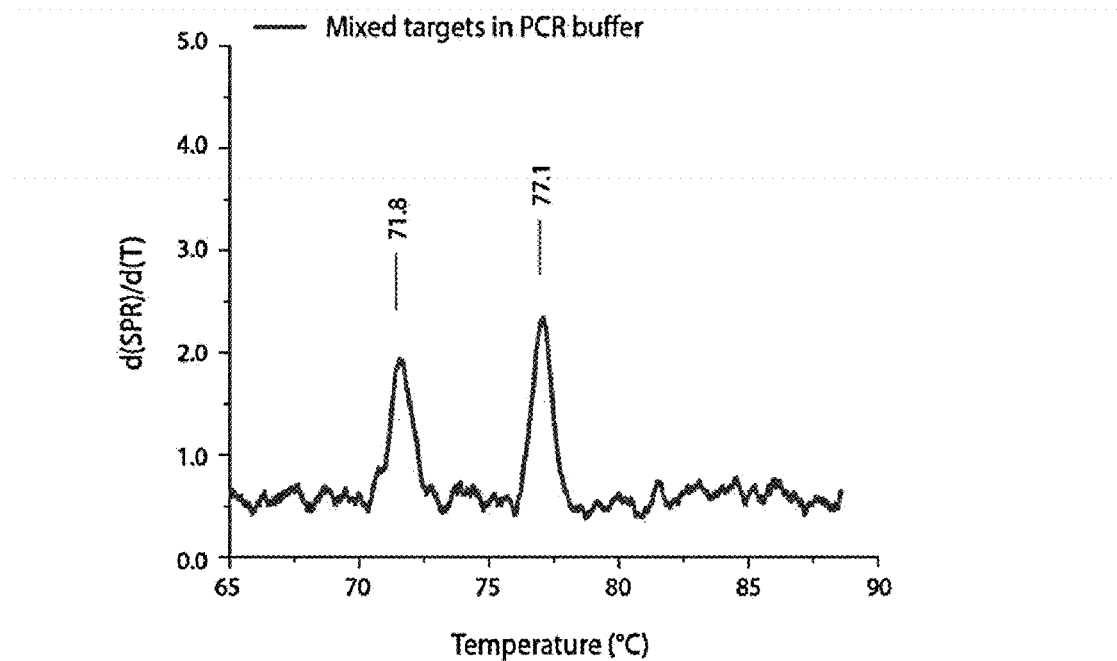

FIG. 11 shows multiplex FO-SPR melting analysis for the MAP (*Mycobacterium avium* subspecies *paratuberculosis*) and *Mycobacterium bovis* target sequence performed in PCR buffer.

Figure 12:
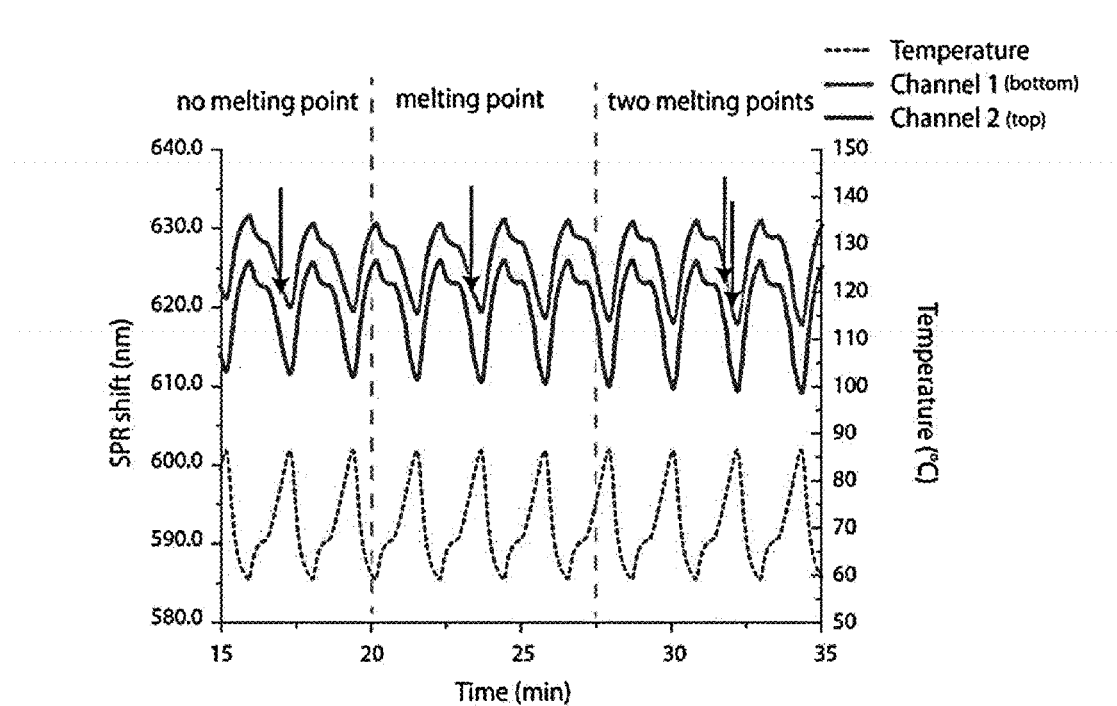

FIG. 12 shows raw data of an FO-SPR PCR measurement. Two measurement channels (channel 1 and channel 2) measure continuously changes in refractive index due to the thermocycling. As a result, the FO-SPR signal is the inverse of the temperature measured with a thermocouple. From the moment a target DNA species is present, the FO-SPR signal will obtain a characteristic melting point of the particular DNA target, which is superimposed on the FO-SPR signal of the temperature shift.

Figure 13:
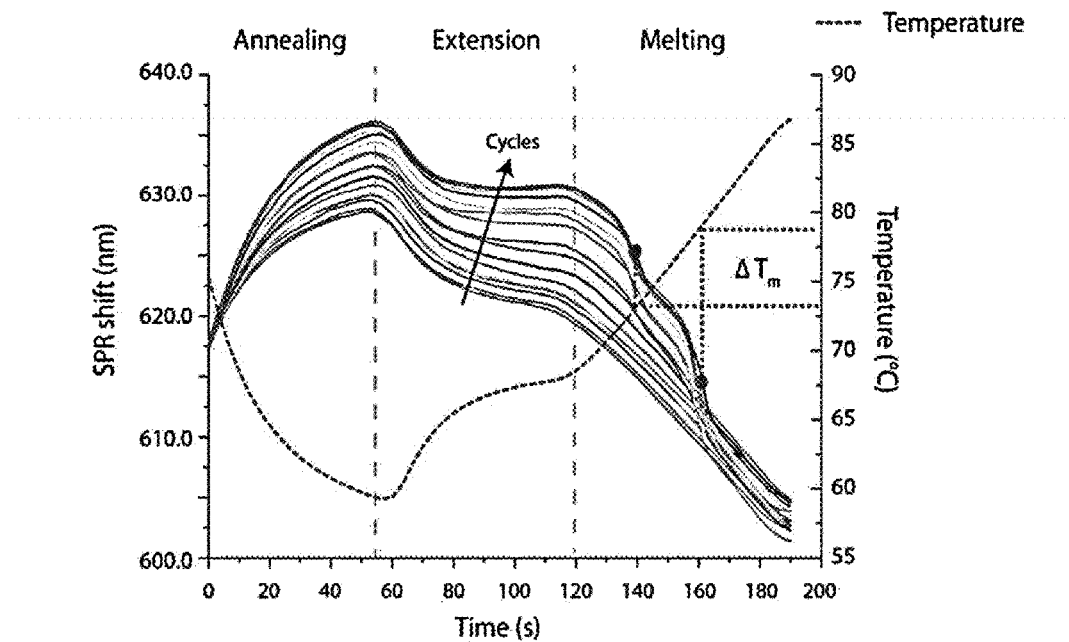

FIG. 13 shows the FO-SPR signal for each PCR cycle (represented with differently lines, increasing with each cycle) in a multiplex PCR reaction containing bacterial DNA of both MAP (*Mycobacterium avium* subspecies *paratuberculosis*) and *Mycobacterium bovis* at a concentration of 1 nM. Initially, the FO-SPR signal is the exact inverse of the temperature signal. When DNA reaches the detection limit of the FO-SPR sensor, a melting signal for each DNA target becomes visible.

Figure 14:
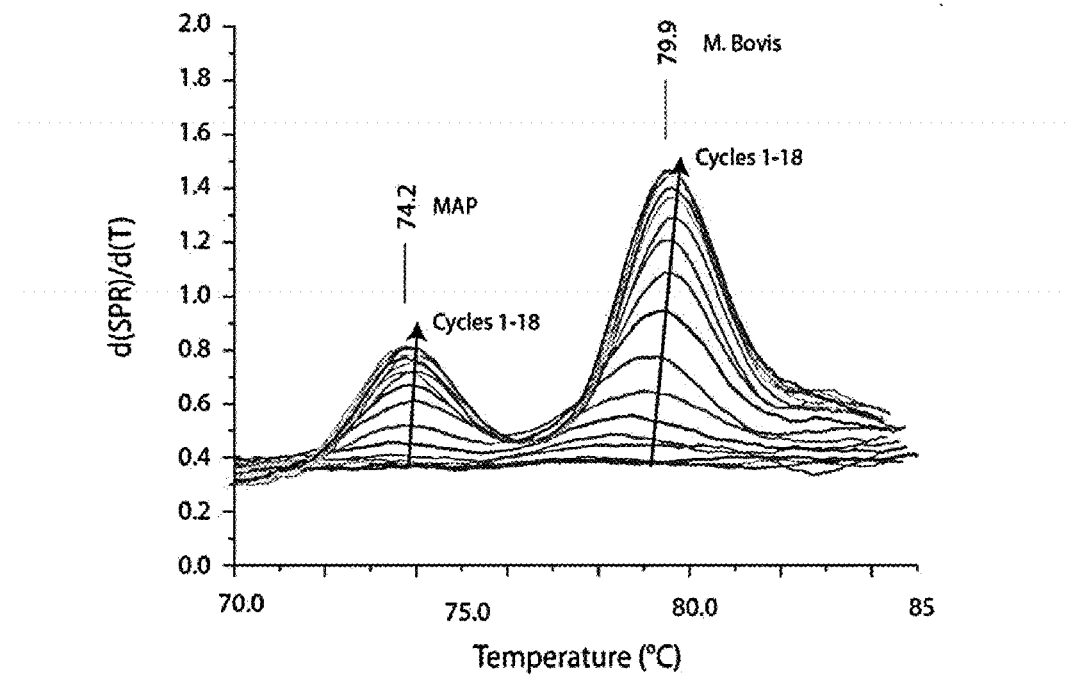

FIG. 14 shows the first order derivative of the FO-SPR signal and temperature, which allows resolving the melting point of the two target DNA types amplified with the multiplex PCR. The MAP sequence has a lower melting point, because it is considerably shorter. Both targets can easily be resolved as the signals are separated by 5.7° C. The different lines indicate the individual PCR cycles used to amplify the target DNA, and increase with each cycle. From these curves the DNA quantity can be derived.

Figure 15:
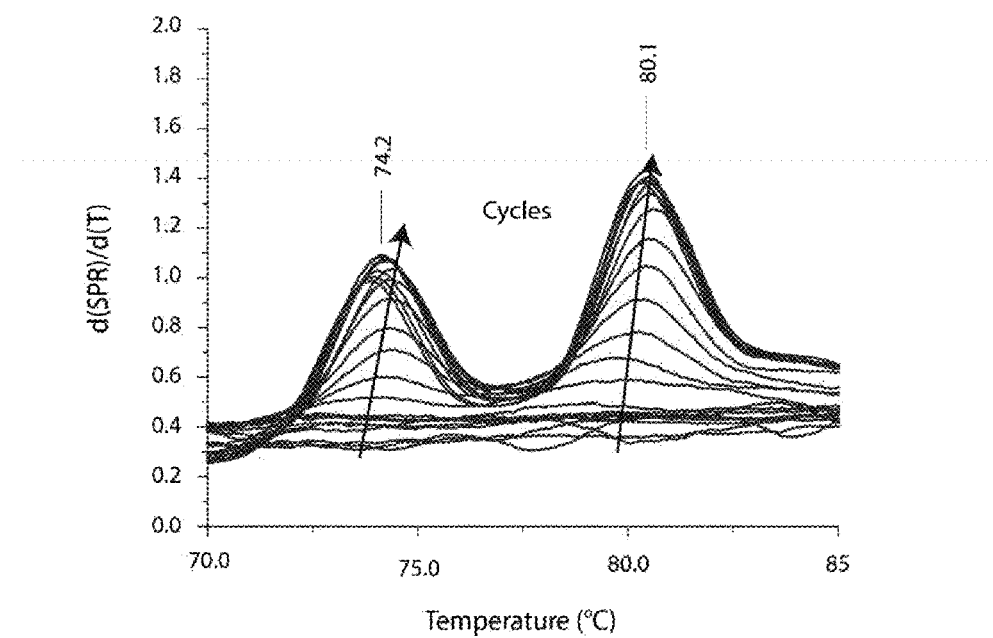

FIG. 15 shows the FO-SPR PCR analysis of the wild type MAP and *M. bovis* target sequences at a concentration of 10 pM. Again the different curves represent the signal for each PCR cycle. With increasing numbers of PCR cycles a better melt signal is obtained.

Figure 16:
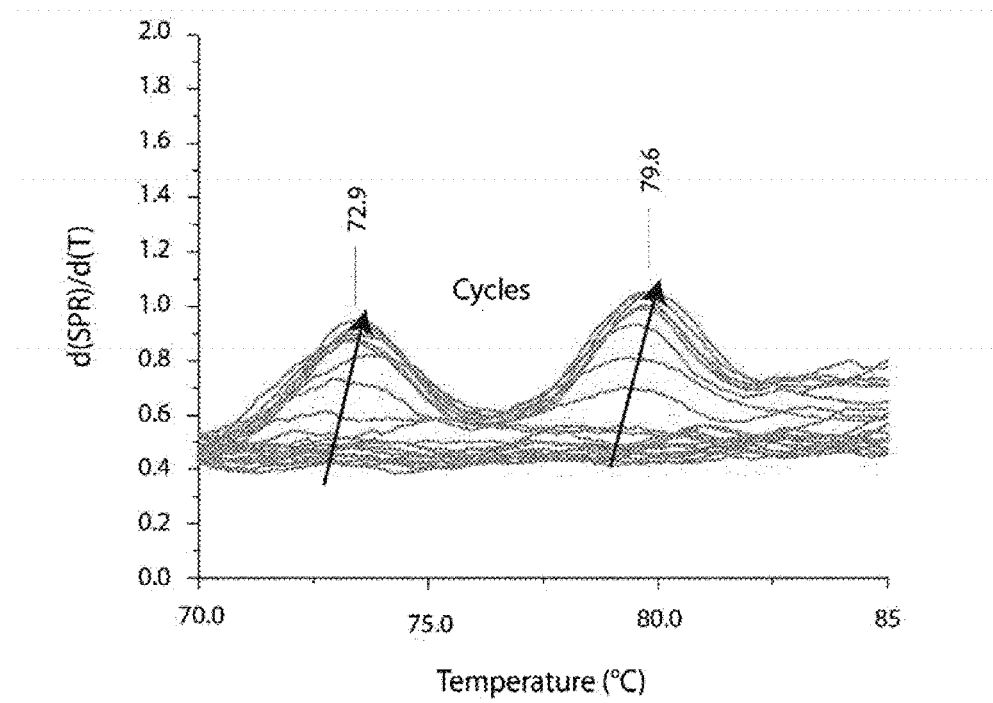

FIG. 16 shows the FO-SPR PCR melting analysis of MAP and *M. bovis* sequences bearing a single SNP (MM1MAP and MM1BOV).

Figure 17:
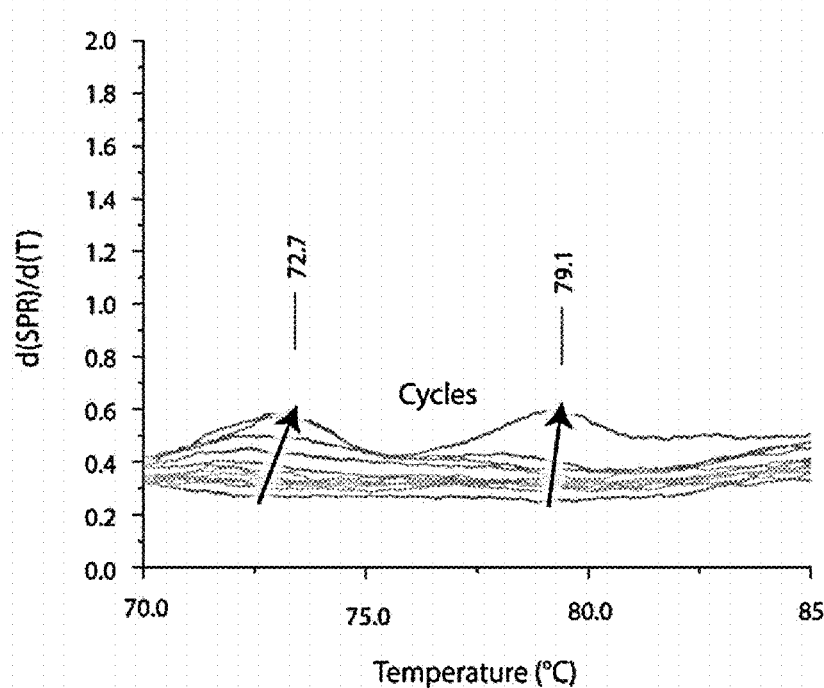

FIG. 17 shows the FO-SPR PCR melting analysis of MAP and *M. bovis* sequences bearing triple mutations (MM3MAP and MM3BOV).

Figure 18:
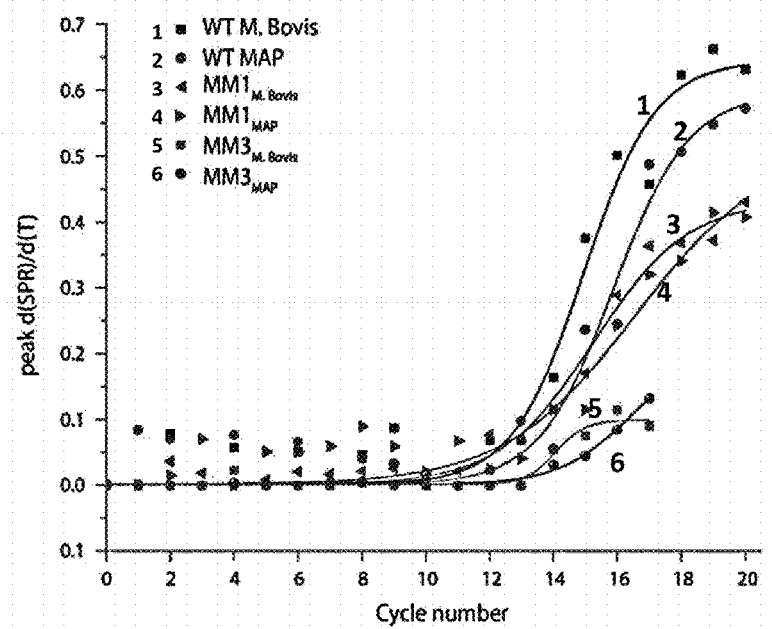

FIG. 18 shows a plot of the height of the FO-SPR obtained melting peak versus the PCR cycle numbers. From this graph it can be seen that mismatches in the target sequence shift the cycle threshold to a higher value and that the final yield of the PCR reaction is lower.

DETAILED DESCRIPTION OF THE INVENTION

"Sensor" in the context of the present invention relates to the part of a sensing device to which nucleic acids probes are bound, and where the presence or absence of a further nucleic acid, hybridized to the bound probe can be determined. This is the part of the sensor which is submerged in the reaction chamber when the reaction is performed. This part also called "sensor tip" is typically provided as a ready to use kit component which is connected to the sensing device.

"amplification in solution" refers to methods wherein the primers for amplification are not bound to the sensor surface. The primers are typical DNA oligonucleotides with unmodified phosphate and hydroxyl groups at respectively 5' and 3' end. This in contrast with "solid phase amplification" wherein one primer is coupled to the sensor surface.

The present invention relates to methods for detection, identification, and quantification of multiple nucleic acids, in real-time and, using nucleic acid amplification reactions in solution in combination with biosensors.

Biosensors may be used for multiplex target analysis, in particular, to identify target nucleic acids on the basis of their annealing properties with complementary nucleic acid sequences. Melting temperature analysis is effective because target nucleic acids that differ by a single base pair can be distinguished by measuring the temperature at which each target melts or denatures from complementary primers and/or probes. Described herein are methods of melting temperature analysis which use FO-SPR devices and nucleic acid amplification methods which confer several distinct advantages over previous methods: high-resolution melting temperature analysis is conducted in real-time, no fluorescent dyes are used, multiple targets may be identified in the same reaction, targets may be quantified, and the amplification reactions may be performed in solution, i.e. the primers for amplification are not bound to the sensor surface.

A particular advantage compared to Knez et al. cited above is that amplified target is measured during the amplification reaction itself making an integrated real time assay wherein the presence and concentration of amplified target nucleic acid can be assayed cycle by cycle. This makes it possible to stop the assay as soon as a significant amount of target nucleic acid is obtained.

A particular advantages compared to Pollet et al. cited above is that the amplification in solution allows to use probes, different from the primers, to obtain the bending melting at the sensor surface. By selecting length and GC content of the probes a specific melting temperature of choice can be obtained, whereas the melting temperature of the solid phase amplicons in Pollet is defined by the sequence of the entire amplicon.

Biosensors and Nanoparticles

Biosensors combine biologically-derived materials such as nucleic acids with physicochemical detectors. Target analytes interact with the biologically-derived material, and signals are transformed by the physicochemical detectors into a form that is easily measured and quantified. An exemplary biosensor that has been adapted for nucleic acids is an optical biosensor based on the phenomenon of surface plasmon resonance (SPR). Methods described herein are based on fibre optic SPR (FO-SPR) devices. The methodology of quantifying nucleotide targets by cycle to cycle melting peak analysis can be applied to all types of mass based sensors. Basically, the sensor has to be capable to detect the presence of a nanoparticle near to a surface because of DNA interactions and to allow accurate temperature control. Examples of capable technologies are including but not limited to Quartz crystal microbalance, (micro/nano) Cantilevers, Acoustic wave, (Young) Interferometry, Surface plasmon resonance, Frustrated total internal reflection, Photonic crystal nanowire, suspended microchannel resonator, Giant magneto resistive sensor, photonic ring resonator.

Any sensor based on mass detection of nucleic acids directly or via the direct or indirect binding of another mass element are applicable in the context of the present invention.

Nanoparticles are mass elements used to increase sensitivity of binding assays. In biosensors, nanoparticles enhance the signals which are detected and transformed by physiochemical detectors. Gold nanoparticles (Au NPs) are well-suited for use with FO-SPR devices, as are other metal nanoparticles comprising silver, copper, platinum, ruthenium, and palladium, or a combination of metals. Exemplary metal nanoparticles used for the methods described herein may have a diameter between 2 and 100 nm.

FO-SPR Methods

Annealing (hybridization) and denaturation (melting) of the target nucleic acids and the complementary sequences are measured at the sensor during the amplification process. After each amplification round amplified DNA is denatured by heating. Upon cooling of the denatured sample part of the amplified DNA will hybridise with the amplification primers in solution and part of the DNA will form a complex with the first probe on the sensor surface and the second probe on the metal particle. This complex formation brings the metal particles in the proximity of the sensor surface. On the FO sensor, a refractive index signal is measured by superimposing the specific binding signal of nanoparticles to the FO sensor over the refractive index shift caused by the change in temperature. If the molecular weight of the interacting compounds and the amount of ligand that covers the sensor surface are known, stoichiometry is determined by comparing the expected spectral response in resonance units, (RU-exp), with the observed one, (RUobs). This assumes that the refractive index increments, dn/dC, are similar for all molecules, where n is the refractive index at the surface and C is the concentration of one compound.

Target nucleic acids bound to the nanoparticles are identified by refractive index shifts at specific temperatures, which depend on the length and base pair composition (GC versus AT content) of the target sequence. There is a narrow temperature distribution at which the target nucleic acid sequences will melt from their complementary probes. Accordingly, in some embodiments, the specific temperatures at which measurable shifts in the refractive index occur correspond with melting temperatures at which each target nucleic acid separates from its complementary nucleic acid probes. In certain embodiments, measurable shifts in the refractive index are compared with a calibration curve indicating expected melting temperatures for each target nucleic acid. The experimental measure of a candidate target is thereby referenced with a standard measurement established for a known nucleic acid sequence, and a match between the candidate and the standard confirms the identity of the target. Conversely, a mismatch between the candidate and the standard confirms that the target is different from the standard.

The formation of the complex between target nucleic acid first probe and second probe is obtained by two binding events, the first one between the first probe (P1) and part of the target NA (P1-NA'), the second one between the second probe (P2) and another part of the NA (P2-NA"). Upon heating of the sample and melting of the complex is it the lowest melting temperature of the complexes (P1-NA and P2-NA") in the methods of the present invention, which will be decisive for the release of the metal particle from the sensor.

If the melting temperature of P2-NA" is the lowest, the first event that happens is the release of P2 while the nucleic acid is still bound to P1 on the sensor. The metal particle on P2 is set free from the sensor surface resulting in a measurable shift If the melting temperature of P1-NA' is the lowest, the first event that happens is the release of the nucleic acid with P2 still bound to it. Nevertheless the metal particle on P2 is also released from the sensor surface resulting in a measurable shift.

The methods of the present invention allow the quantification of the target nucleic acids. In some embodiments, quantities of each target nucleic acid are determined in real-time by measuring amplification cycles needed to produce the measurable shift in refractive index. A refractive index shift is measurable when a sufficient quantity of the target nucleic acid has bound to, or melted from the probes on the metal nanoparticles. Thus, the concentration of nucleic acid in a sample depends on the number of amplification cycles required to produce sufficient copies to bind to, or melt from, the probe-functionalized nanoparticles and mediate a refractive index shift. Amplification cycles may be repeated until a shift in the refractive index is first obtained, and repeated to collect additional data points. For samples containing multiple target sequences, a melting curve may be generated which reflects multiple melting points dependent on the number of target sequences. In some embodiments, the number of amplification cycles is compared with a reference curve indicating nucleic acid concentration as a function of amplification cycles.

In some embodiments, for example in PCR reactions, the amplification cycles comprise a denaturation (or melting) step, an annealing (or hybridization) step, and an elongation (or extension) step. In certain embodiments, for example for LCR reactions, the amplification cycles comprise an annealing (or hybridization) step, a ligation step, and a denaturation (or melting) step. The refractive index at the FO sensor may be continuously measured during all of the amplification cycles of the nucleic acid amplification reaction. In some embodiments, the refractive index at the FO sensor is measured during at least one of the denaturation phase, annealing phase, or an elongation phase of an amplification cycle. The measurements may be performed at each of the amplification cycles, or at one or more of the amplification cycles. Typically the measurement is performed in a temperature segment encompassing the melting temperature to be considered during the denaturation step of the amplification methods.

A number of parameters in the nucleic acid amplification reactions may be varied in the detection and quantification methods described herein. The number of amplification cycles may be varied. In some embodiments, the amplification reactions comprises at least 5 amplification cycles. In certain embodiments, the amplification reactions comprise between 5 and 65 amplification cycles, for example, 5, 10, 15, 20, 25, 30, 35, 40, 45, 50, 55, 60, or 65 amplification cycles. In some embodiments, the amplification reactions comprise at most 65 amplification cycles. Because the methods of the present invention provide the possibility to measure in real-time, cycle by cycle, the presence of amplified target DNA, it is possible to stop the amplification when a significant result is obtained.

The rate at which temperatures are changed during the amplification cycles affects the speed and resolution of the detection and quantification methods. In some embodiments, the ramp speed is varied. Ramp speed is the rate at which sample temperature is changed, this is aimed at all steps in the amplification cycles where temperature changes occur. In practice, ramp speeds should be as high as possible (depending on device and biological compounds) during amplification to obtain a shorter assay time.

The present invention combines nucleic acid amplification methods with real time melting temperatures analysis during amplification, and this within the same reaction vial. Amplification reactions, and especially PCR reaction try to optimize and minimize the duration of annealing extension and denaturation step. Since the melting temperature analysis is typically performed during the denaturation step, PCR protocols may be adapted by changing the ramp speed of the denaturation step.

In certain embodiments, melting rates are varied. Melting rates refer to the temperature changes occurring specifically during the denaturation step. In melting analysis, the melting rates are crucial as they have to be low enough for a high melting resolution. Exemplary melting rates should be around 1° C./s. Melting rates of this speed may be performed during PCR or other nucleic acid amplification reactions. In some embodiments, melting rates are 10 times slower, for example, 0.1° C./s, to obtain a higher melting resolution.

In standard PCR reactions, for example, the ramp speeds during the denaturation, annealing, and elongation steps are typically 1° C./s to 8° C./s, which leads to rapid amplification of target sequences. In some embodiments, the ramp speeds are in the range of 1° C./s to 8° C./s, for example 1° C./s, 2° C./s, 3° C./s, 4° C./s, 5° C./s, 6° C./s, 7° C./s or 8° C./s. In some embodiments, ramp speeds may have a maximum ramp speed of 30° C./s.

However, resolution may be improved in the disclosed methods when the melting rates of the nucleic acid amplification reactions were faster, in the range of 0.1° C./s-1.5° C./s. Accordingly, in some embodiments the methods may be performed with a melting rate of 0.1° C./s, 0.2° C./s, 0.3° C./s, 0.4° C./s, 0.5° C./s, 0.6° C./s. 0.7° C./s, 0.8° C./s, 0.9° C./s, 1.0° C./s, 1.1° C./s, 1.2° C./s, 1.3° C./s, 1.4° C./s, or 1.5° C./s. In certain embodiments, the melting rate is 0.2° C./s. In certain embodiments, the melting rate is 1.0° C./s. In certain embodiments, melting rates are in the range between 0.7° C./s and 1.2° C./s, for example, 0.7° C./s, 0.8° C./s, 0.9° C./s, 1.0° C./s, 1.1° C./s, or 1.2.° C./s. In certain embodiments, the amplification cycles comprise at least 1 cycle in which the melting rate is in the range of 0.1° C./s-1.5° C./s. In some embodiments, the amplification cycles comprise at most 50 cycles in which the ramp speed is in the range of 1.0° C./s-8.0° C./s. The amplification cycles may comprise cycles in which faster and slower ramp speeds are alternated. An exemplary amplification reaction may comprise up to 50 cycles in which ramp speeds are between 1.0° C./s-8.0° C./s and, optionally, melting rates in at least one cycle are in a range between 0.1° C./s-1.5° C./s. Notably, the ramp speeds may also vary within an amplification cycle, so that the ramp speed during the denaturation, annealing, and elongation steps are different. The reaction may be monitored during all steps in the amplification cycle, or may be monitored only during the melting step at melting rates within the range of 0.1° C./s-1.5° C./s.

The duration of the denaturation, annealing, and elongation steps of the nucleic acid amplification reaction also affect the speed and resolution and may be varied in the methods disclosed herein. In some embodiments, at least one amplification cycle comprises an initial denaturation step of less than 10 minutes in duration. All other amplification cycles may comprise the same denaturation step of less than 5 seconds. In certain embodiments, at least one amplification cycle comprises an elongation step of at least 10 seconds in duration. In some embodiments, at least one amplification cycle comprises an elongation step of at least 20 seconds in duration. In some embodiments, the elongation step is no more than more than 60 seconds in duration. PCR reactions may combine annealing and elongation steps into 1 step. Accordingly, the combined step may be as short as 10 seconds.

In certain embodiments, a method for real-time detection and/or quantification of two or more target nucleic acids in a solution comprises (a) obtaining a fibre optic (FO) sensor functionalized with a first set of nucleic acid probes; (b) obtaining metal nanoparticles each functionalized with a second set of nucleic acid probes; (c) combining the sample with nucleic acid primers in solution whose sequences are complementary to the two or more target nucleic acids; (d) conducting PCR comprising amplification cycles to amplify the two or more target nucleic acids in the presence of the FO sensor, metal nanoparticles, and nucleic acid primers, wherein the amplification cycle is held for at most 60 seconds at a temperature during an elongation step and held less than 1 second at a temperature during a denaturation step; and (e) measuring a refractive index at the FO sensor during the PCR; wherein measurable shifts in the refractive index at specific temperatures reached during the PCR indicates the presence of each of the two or more target nucleic acids.

In certain embodiments, a method for real-time detection and/or quantification of two or more target nucleic acids in a solution comprises (a) obtaining a fibre optic (FO) sensor functionalized with a first set of nucleic acid probes; (b) obtaining metal nanoparticles each functionalized with a second set of nucleic acid probes; (c) combining the sample with nucleic acid primers in solution whose sequences are complementary to the two or more target nucleic acids; (d) conducting LCR comprising amplification cycles to amplify the two or more target nucleic acids in the presence of the FO sensor, metal nanoparticles, and nucleic acid primers, wherein the amplification cycle is held at a probe hybridization temperature for at most 3 minutes, a ligation temperature for at most 3 minutes, and a denaturing temperature for at most 5 seconds; and (e) measuring a refractive index at the FO sensor during the LCR; wherein measurable shifts in the refractive index at specific temperatures reached during the LCR indicates the presence of each of the two or more target nucleic acids.

In some embodiments, during LCR, the amplification cycle is held at the probe hybridization temperature for at most 3 minutes at approximately 35° C., the ligation temperature for at most 3 minutes at approximately 42.5° C., and the denaturing temperature for at most 5 seconds at approximately 70° C.

Nucleic Acid Amplification Reactions

A variety of nucleic acid amplification reactions may be integrated into the methods described herein. Any amplification method which uses non-isothermal amplification cycles can be used. Typically the nucleic acid amplification method is performed by polymerase chain reaction (PCR), or ligation chain reaction. Specific variants hereof are asymmetric PCR, hot start PCR, inverse PCR, ligation mediated PCR, methylation specific PCR, miniprimer PCR, multiplex ligation-dependent probe amplification, multiplex PCR, nanoparticle-assisted PCR, nested PCR, quantitative PCR, reverse transcription PCR, suicide PCR, thermal asymmetric interlaced PCR, touchdown PCR 1, multiple-displacement amplification, linear DNA amplification, T7-based DNA linear amplification, and nucleic acid sequence based amplification.

Polymerase Chain Reaction (PCR)

In certain embodiments, the nucleic acid amplification reaction is PCR. DNA may be amplified by PCR, or RNA may be amplified by RT-PCR. PCR reactions typically comprise a thermostable polymerase. In an exemplary DNA amplification reaction, the amplification cycles may comprise a denaturation step, an annealing step, and an elongation (or extension) step. Reactions may also comprise a denaturation step and an annealing step.

Accordingly, one aspect of the present disclosure relates to a method for real-time detection of two or more target DNA sequences in a solution, comprising obtaining a fibre optic resonance (FO) sensor functionalized with a first set of nucleic acid probes; obtaining metal nanoparticles each functionalized with a second set of nucleic acid probes; combining the sample with nucleic acid primers in solution whose sequences are complementary to the two or more target DNA sequences; conducting PCR comprising amplification cycles to amplify the two or more target DNA sequences in the presence of the FO sensor, metal nanoparticles, and nucleic acid primers; and measuring refractive index at the FO sensor during PCR; wherein measurable shifts in the refractive index at specific temperatures reached during PCR indicates the presence of each of the two or more target DNA sequences. In some embodiments, the method is also used for quantification of the target DNA sequences, as the quantities of each target DNA are determined in real-time by measuring PCR amplification cycles needed to produce the measurable shift in refractive index.

In some embodiments, a method of real time monitoring of amplification of a target nucleic acid sequence in a biological sample, comprises the steps of (a) amplifying the target sequence with PCR in the presence of oligonucleotide functionalized metal nanoparticles; wherein the PCR comprises the steps of adding oligonucleotide functionalized metal nanoparticles, a thermostable polymerase, and primers for the target nucleic acid sequence to the biological sample to create an amplification mixture and thermally cycling the amplification mixture between at least a denaturation temperature and an elongation temperature during a plurality of amplification cycles under conditions wherein the oligonucleotide functionalized metal nanoparticles retains the ability to produce a refractive index signal related to the quantity of the nucleic acid sequence; (b) inserting a fibre optic sensor functionalized with a nucleotide to monitor refractive index changes in the biological sample comprising the target nucleic acid sequence detecting the hybridization and denaturation of the nucleotide functionalized metal nanoparticles subsequent to at least a portion of the plurality of amplification cycles; and (c) monitoring refractive index signals from the oligonucleotide functionalized metal nanoparticles in the sample as a function of sample temperature to generate a melting curve for the amplified target sequence. In some embodiments, the PCR reactions are cycled between at least a denaturation temperature and an annealing temperature. In some embodiments, 30 amplification cycles are completed in 10 to 60 minutes.

In certain embodiments, a method for monitoring the amplification of a nucleic acid in a biological sample during PCR comprises the steps of (a) forming an amplification mixture comprising the biological sample, a metal entity capable of producing a refractive index signal related to the amount of nucleic acid present in the sample, a thermostable polymerase, and primers for the nucleic acid, (b) amplifying the target sequence by thermally cycling the amplification mixture through a plurality of thermal cycles; and (c) probing the sample with an optical fibre functionalized with a first set of oligonucleotide probes and monitoring the refractive index signal from the metal entities functionalized with a second set of oligonucleotide probes which hybridize to the optical fibre by their target oligonucleotides during amplification. A metal entity such as monodisperse nanoparticles comprising gold, silver, copper, palladium, or platinum, within a 2-100 nm diameter size, and the metal entity may be functionalized with a set of oligonucleotide probes. The complex formation between the optical fibre and the metal entities by hybridization and denaturation of the generated amplicons is monitored, thus leading to fast monitoring of sharp melting profiles of the functional metal nanoparticles during each amplification cycle.

Ligation Chain Reaction (LCR)

Figure 1:
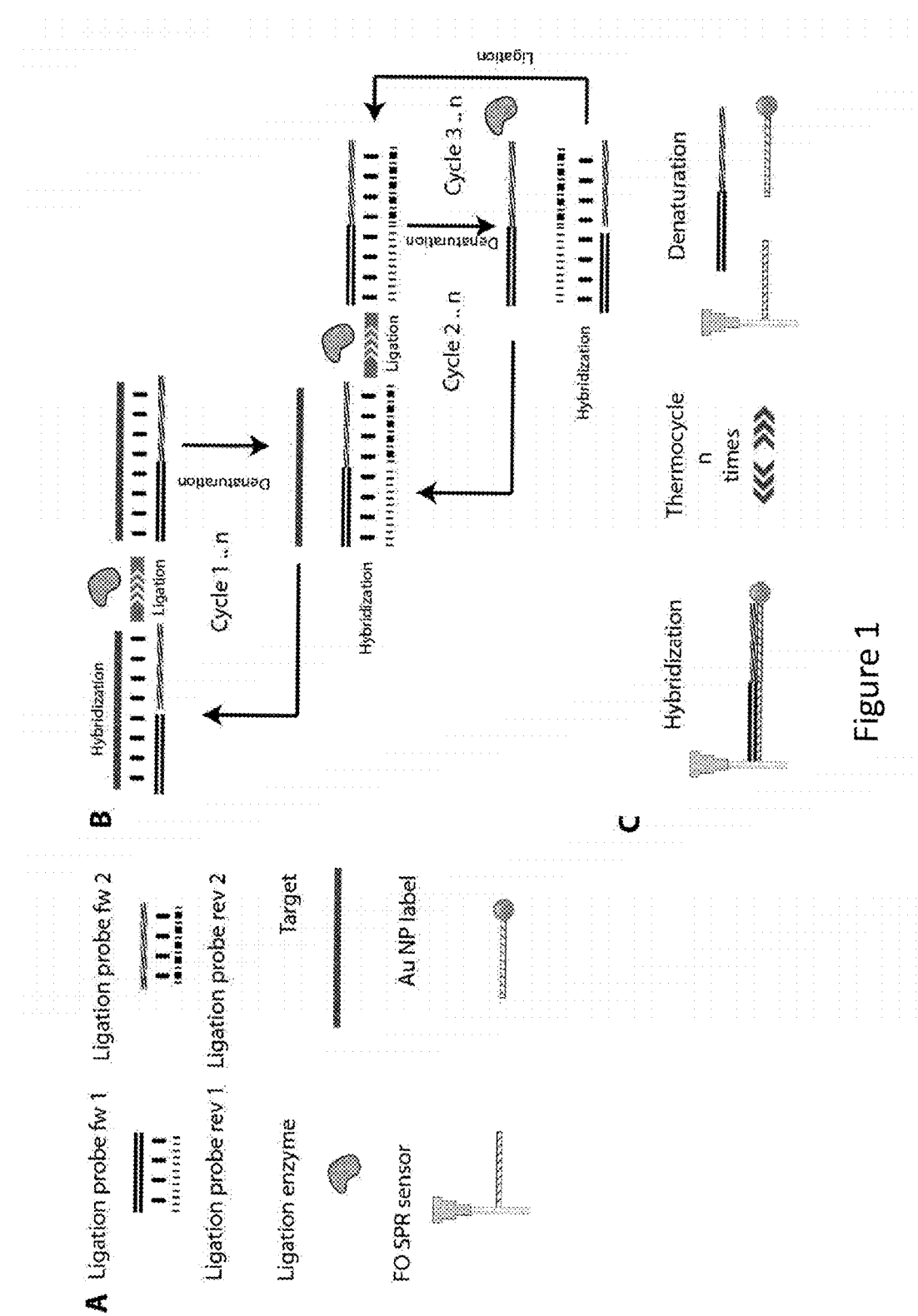
FIG. 1 shows a schematic overview of FO-SPR LCR. A.) Different components of the reaction. B.) LCR reaction where the forward (fw) and reverse (rev) probes are ligated only in the presence of the target sequence, resulting in an exponential amplification during multiple thermal cycles. C.) The forward LCR product can, during the LCR reaction, form a complex with two complementary probes immobilized on the FO-SPR sensor and on Au NPs, allowing real-time monitoring of the reaction by means of its reaction products.

In Ligation Chain Reaction (LCR), DNA is amplified exponentially, much in the same way as in the PCR reaction. However, a thermophilic ligation enzyme is used to covalently bind the phosphorylated 5' end of one DNA strand with the 3' end of another strand, these hybridization probes, are only ligated when they are hybridized to a perfectly matching target sequence (FIG. 1, part B). In this way, multiple DNA probes can be linked together even when only one target strand is present, as the complex formed between ligated probes and target is denatured at a temperature above its melting temperature ($T_m$), liberating target strands for the multiple subsequent ligation cycles. The reaction results in an exponential amplification, as each ligated target will function as a template for ligation of reverse probes complementary to the original ligation probes.

In recent studies, LCR was combined with Au NPs by linking DNA probes immobilized on Au NPs only in the presence of the target sequence. As a result, an increasing amount of Au NPs irreversibly aggregated with increasing number of ligation cycles, causing a gradual shift in the absorbance of the Au NP solution due to LSPR adsorption band coupling. The assay could quantify the initial target concentration by determining the number of ligation cycles necessary to generate a colorimetric change in the Au NP solution [Shen et al. *J. Am. Chem. Soc.*, 2012, 134, 14678-14681; Shen et al., *Chem Co mMun (Camb)*, 2012, 48, 10225-10227].

As disclosed herein, the FO-SPR sensor-based methods for nucleic acid detection and quantification may comprise Au NPs and LCR. The FO-SPR sensor replaces the colorimetric read-out of earlier studies, increasing assay sensitivity [Lyon et al., *Anal. Chem*, 1998, 70, 5177-5183]. Probes are ligated in free solution instead of on Au NPs, and the ligation product is hybridized to complementary probes immobilized on both the Au NP surface and the FO-SPR sensor surface (FIG. 1). Each cycle of the LCR reaction results in more ligated probes, allowing more Au NPs to bind to the FO-SPR, thereby increasing the FO-SPR signal from cycle to cycle. LCR products may be quantified by counting the number of cycles necessary to reach the amplification threshold. Moreover, the Au NP-ligated probe complex formed on the FO-SPR surface was melted during each LCR cycle, allowing identification of the amplified strands during the LCR reaction. Hence, in the methods disclosed herein, in contrast to the use of Au NPs in earlier LCR assays which depend on an irreversible aggregation of the nanoparticle complexes, Au NPs may be used were used to their full potential as labels in melting analysis and identification of the amplified targets [Jin et al., *J. Am. Chem. Soc.,* 2003, 125, 1643-1654].

In certain embodiments, the FO-SPR melting assay is integrated with the LCR reaction. Mutations in the nucleic acid sequences which lie in close vicinity to the ligation site will inhibit the ligation reaction. Thus, in some embodiments, each target nucleic acid that contains mutations in or near the ligation site has a new set of hybridization probes. For example, a method for real-time detection of two or more target nucleic acids in a solution, comprising obtaining a fibre optic surface plasmon resonance (FO) sensor functionalized with a first set of nucleic acid probes; obtaining metal nanoparticles each functionalized with a second set of nucleic acid probes; combining the sample with nucleic acid primers in solution whose sequences are complementary to the two or more target nucleic acids; conducting LCR comprising amplification cycles to amplify the two or more target nucleic acids in the presence of the FO sensor, metal nanoparticles, and nucleic acid primers; and measuring a refractive index at the FO sensor during LCR; wherein measurable shifts in the refractive index at specific temperatures reached during LCR indicates the presence of each of the two or more target nucleic acids.

Reaction Conditions

The reaction conditions for PCR and LCR reactions are linked to the target and to the FO-SPR sensor. The reactions are very sensitive to changes in temperature. If temperatures are too low, this leads to non-specific binding while temperatures that are too high inhibit nanoparticle binding. For example, during PCR primer annealing is kept near the primer melting temperature (for instance 62° C.). During LCR primer annealing is kept near their hybridization temperature (for instance 35° C.). Higher temperatures result in lower nonspecific hybridization and thus a more specific amplification, but lower amplification efficiencies.

Surfactants are used to keep the nanoparticles in suspension during the reactions, for example 1% w/v Triton X. However, surfactant concentrations that are too high will influence diffusion of the nanoparticles.

In addition, a low salt concentration may inhibit hybridization of the nanoparticles to the FO-SPR sensor, while a high salt concentration may inhibit the amplification process. In some embodiments, the PCR reaction of the disclosed methods is conducted in solution containing NaCl. For example, the solution contains NaCl in a concentration between 10 mM-50 mM. The solution may also contain $MgCl_2$, in a concentration of between 1 mM-3 mM $MgCl_2$. An exemplary PCR reaction as described herein may be conducted at 2 mM $MgCl_2$ and 20 mM NaCl.

In LCR, monovalent salt and divalent salt concentrations affect the ligation yield, as well as the stability and aggregation properties of Au NPs. In some embodiments, the LCR reaction of the disclosed methods is conducted in a solution containing 600 mM NaCl and 25 mM $MgCl_2$. The reaction solution may not contain DTT.

The quantities of nucleic acid probes which functionalize the FO-SPR sensors affect the progress of the amplification reaction. High concentrations of nucleic acid probes cause the polymerase to stick to the FO-SPR sensor and inhibit the PCR reaction. Conversely, low concentrations of nucleic acid probes may not be sufficient for hybridization and detection of targets at the FO-SPR sensor. In some embodiments, nucleic acid probes such as DNA are densely packed on the surface of the FO-SPR sensor, and then partly displaced with a PEG molecule, which also prevents non-specific binding to the FO sensor.

Nucleic Acid Probes and Primers

The methods comprise a first and a second set of nucleic acid probes, as well as nucleic acid primers. In some embodiments, the first set of nucleic acid probes comprises oligonucleotides whose sequences are complementary to a first strand of each target nucleic acid. In certain embodiments, the second set of nucleic acid probes comprises oligonucleotides whose sequences are complementary to a second strand of each target nucleic acid. In some embodiments, the nucleic acid primers comprise oligonucleotides whose sequences are complementary to a first strand of each target nucleic acid and oligonucleotides whose sequences are complementary to a second strand of each target nucleic acid.

In some embodiments, probes and primers are configured for amplification of the target nucleic acid sequence, and are complementary to at 15-200 base pairs of the target. Probes may hybridize a part of the amplicon to allow modulation of the melting temperature within the range of 60-95° C. Several probes for different target amplicons may be designed, each with a distinct melting temperature so that multiple target sequences are differentiated within one reaction and are quantified in real-time.

Target Nucleic Acids

Target nucleic acids can be short oligonucleotides of 15-80 base pairs, or longer nucleotides (including PCR amplicons) ranging from 40200 bp, or more. Target nucleic acids may be DNA, RNA, or artificial analogues of nucleotides. The methods described herein may be used for detecting RNA, if combined with a reverse transcriptase assay. RNA may also be detected directly using the melting analysis methods if the concentration of target RNA is high enough.

Target nucleic acids may differ by at least one nucleic acid, such that a first target contains an addition, deletion, or substitution of a nucleic acid as compared with one or more other targets. Targets may contain base pair insertions, frame shifts, or any other types of mutations. Target nucleic acids may contain modified base pairs, and may be methylated. Target nucleic acids may be labeled via the amplification primers with nucleic acid tags which shift the melting temperature, and nano-labels can be incorporated via the amplification primers to amplify the SPR signal. For example, the use of an oligo-T repeat at an end of the primer will reduce the melting temperature. This can be used if neighbouring melting temperatures impede the measurement in a multiplex assay.

In some embodiments, target nucleic acids contain SNPs, and there may be one single SNP or multiple SNPs detected in a target.

The method of the present invention can be applied with one pair of PCR primer pairs to generate an amplified DNA fragment. This can be a primer pair specific for the presence of a pathogen. If the assay is designed to detect the presence/absence of the pathogen, one set of first and second probe is sufficient to perform the assay.

It is also possible to use one PCR primer pair to amplify e.g. a piece of human DNA, wherein one copy of the DNA is WT and the other carries a mutation. In this case two pairs of first and second probes can be used, one pair for the wild type allele, one pair of the mutant allele. The difference in melting temperature caused by the mutation is sufficient to verify carrier or disease status. Alternatively, a mismatch such as a SNP can be detected by one pair of first and second probes, hybridizing at the region of the mismatch. A probe which has a mismatch hybridizes less well and has different measurable melting temperature.

In a similar example, one pair of PCR primers is used which hybridizes with conserved regions in different (e.g. 2, 3, or 5) related bacteria. Different first and second probes are designed for variable regions between the bacterial species.

These are examples to illustrate that one primer pair for amplification can be combined with different first and second probes to determine different target nucleic acids.

In other types of multiplexing assays different sets of primer pairs are used to amplify unrelated DNA regions (eg different fragments of a disease gene, different pathogens causing a similar pathology) with different first and second probes to detect the presence of a specific sequence within the different amplicons.

For example sets of primers can be used to amplify the different exons of BRCA1, whereas different first and second probes are used to detect the presence of specific mutations in the BRCA1 gene which may occur at various positions in the gene.

At least two target nucleic acids can be distinguished from each other and quantified in a single sample. In some embodiments, 2, 3, 4, 5, 6, 7, 8, 9, or 10 or more target nucleic acids may be distinguished and/or quantified.

Samples may be biological samples, and may be turbid media, including fluids obtained directly from test subjects.

Reaction Product Mixtures and Kits

Another aspect of the present disclosure relates to reaction product mixtures materials and kits for use with the methods described herein. Mixtures and kits may contain FO-SPR sensors and metal nanoparticles which have been functionalized, buffers, and, optionally, instructions for use.

In some embodiments, a reaction product mixture comprises an amplified nucleic acid product and oligonucleotide functionalized metal nanoparticles in an amount capable of providing a mass based signal indicative of the concentration of the amplified nucleic acid product in the mixture, the reaction product mixture prepared by subjecting a PCR amplification mixture comprising the target nucleic acid to be amplified, oligonucleotide primers, a thermostable polymerase, and the oligonucleotide functionalized metal nanoparticles, to sufficient thermal cycles to amplify the target nucleic acid. In certain embodiments, a kit for analysis of a nucleic acid sequence during amplification comprises an amplification solution comprising a oligonucleotide functionalized metal nanoparticles selected from the group consisting of gold, silver, copper, palladium, platinum, 2-100 nm diameter size; a thermostable DNA polymerase; and purified deoxynucleoside triphosphates or peptide nucleic acids. In certain embodiments, the kit comprises a pair of primers for amplifying the nucleic acid target sequence.

EXAMPLES

Having provided a general disclosure, the following examples help to illustrate the general disclosure. These specific examples are included merely to illustrate certain aspects and embodiments of the disclosure, and they are not intended to be limiting in any respect. Certain general principles described in the examples, however, may be generally applicable to other aspects or embodiments of the disclosure.

Example 1. Implementation of Ligation Chain Reaction (LCR)

Buffer Optimization

The first step in the implementation of the LCR reaction on the FO-SPR platform was selection of the buffer compatible with both the FO-SPR melting assay and the LCR reaction. The standard ligation buffer supplied by the manufacturer of the ligation enzyme 9° N was not compatible with FO-SPR assay due to the presence of DTT, which reduces thiol bonds essential for immobilization of DNA molecules on gold surfaces. Furthermore, a buffer with certain ionic strength was needed to stabilize the Au NPs and to speed up their hybridization on the FO-SPR surface during the LCR reaction.

Figure 4:
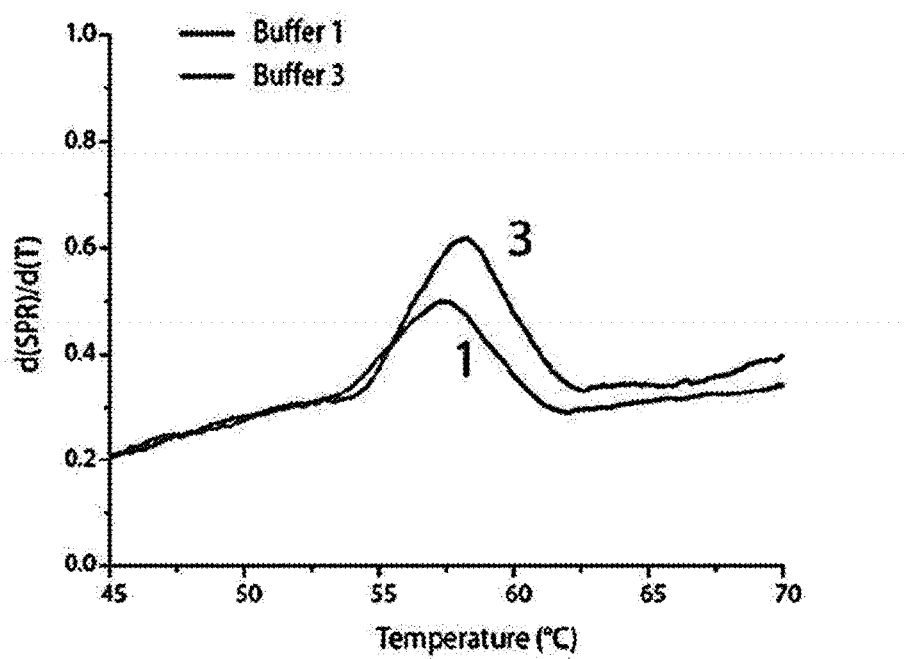
FIG. 4 shows FO-SPR melting analysis of BF Au NPs in two different buffers.

Next, the stability of Au NPs coated with DNA was tested. For this purpose, Au NPs, prepared both with and without backfilling, were compared in LCR, as it is known that backfilled Au NPs should have an increased stability and performance in hybridization assays [Stakenborg et al., Nanopart Res, 2008, 10, 143-152]. When unstable, Au NPs aggregate, which leads to coupling of the LSPR adsorption band of the individual NPs, resulting in a color change of the Au NP solution. Au NP aggregation could by no means be the result of ligation as they only contain a single probe complementary to the target sequence. The best Au NP stability was observed in buffer 3 (100 mM Tris HCL, 6 mM ATP, 25 mM $MgCl_2$, 600 mM NaCl, 1% Triton-X), therefore in a final test, buffer 3 was compared with other buffers to evaluate the performance of the FO-SPR melting assay in these buffers. FIG. 4 summarizes results of the FO-SPR melting assay as described previously for the 30 bp target sequence in the selected buffers. Here buffer 3, which already proved to result in the highest Au NP stability, was also the most suited buffer for the FO-SPR melting assay, as it resulted in the highest melting signal.

DNA Melting Optimization

Figure 5A:
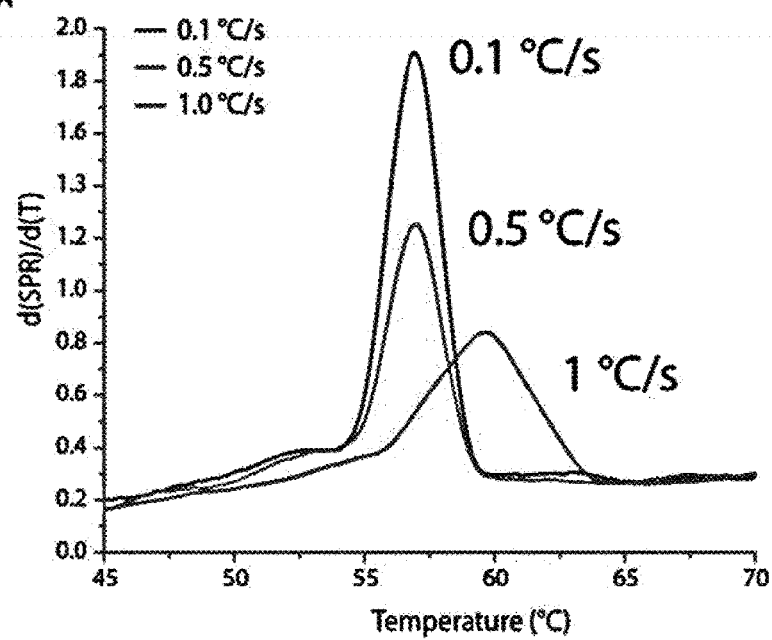
FIGS. 5A-5B shows A) Performance of the FO-SPR melting assay at different temperature ramping speeds. B) FO-SPR melting analysis in the LCR optimal buffer 3 of the wild type (WT) target in comparison with two targets containing a mutation at the 5' or 3' end of the target. The graph represents an overlay of 35 consecutive melting cycles, proving the low variation between assays even after extensive thermocycling.
Figure 5B:
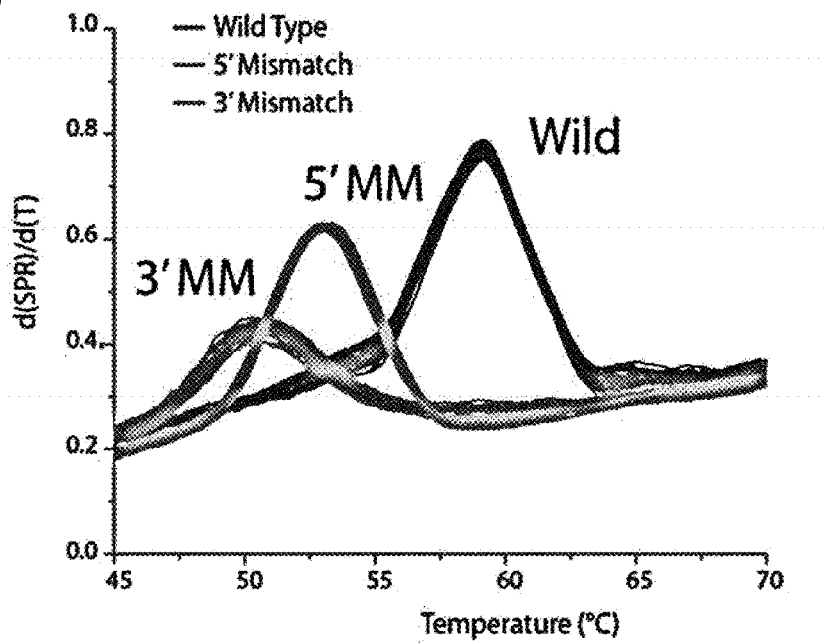

Previously DNA melting analysis was performed at a temperature ramping speed of 0.1° C./s [Knez et al., Small, 2012, 8, 868-872]. However, this ramping speed considerably slows down the LCR reaction and increases the total assay time. Therefore, we evaluated if higher ramping speeds of 0.5° C./s and 1° C./s could result in the same melting resolution. To test this, a melting analysis was performed using the same targets. Results are shown in part A of FIG. 4. As can be expected, the best melting signal was obtained at the slowest ramping speed with almost 2 fold and 3 fold decrease in signal at 0.5° C./s and 1° C./s ramping speeds, respectively. Moreover, at the slowest cycling speed, the inter measurement variability was the lowest (standard deviation obtained on the mean $T_m$ is 0.01° C. for n=4), while with increasing ramping speed this variability increased to 0.1° C. and 0.16° C. for 0.5° C./s and 1.0° C./s ramping speeds, respectively. Furthermore, at 1.0° C./s ramping speed, the melting temperature also shifted to a higher value (from 56.8° C. at 0.5 and 0.1° C./s to 59.5° C. at 1.0° C./s) and the width of the fitted peak of the melting signal considerably increased (from 2.5° C. at 0.5 and 0.1° C./s to 4.2° C. at 1.0° C./s), which could potentially lower the sensitivity of the FO-SPR melting assay and compromise SNP detection. To evaluate this, 30 bp target sequences carrying two SNPs at different positions were compared to the wild type (WT) target of the same size. The acquired melting signal, visualized in part B of FIG. 5, confirmed that even at a 10 fold increased ramping speed, all mutations could clearly be resolved, justifying the choice for 1.0° C./s ramping speed in further experiments. For each FO-SPR melting experiment, 35 consecutive repetitions were performed on the same FO-SPR sensor, to evaluate assay variability. Each cycle consisted of two steps, a first step where the target was allowed to bind for 10 min. followed by a melting step, this resulted in 35 individual melt peaks that had very low variability confirming a good assay performance (FIG. 5 part B).

Example 2: FO-SPR LCR Assay

Figure 6A:
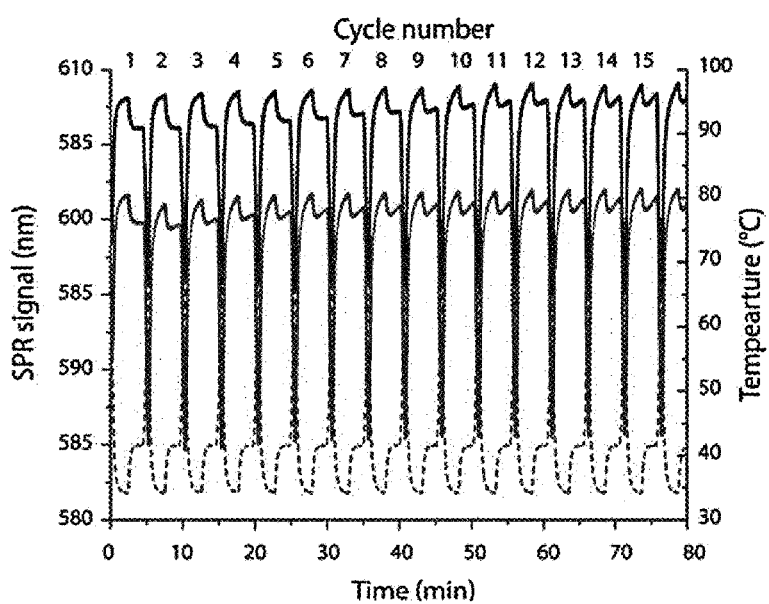
FIGS. 6A-6B shows an overview of typical FO-SPR LCR measurements and data processing performed on the WT target DNA. A) The flow diagram shows the raw signal as measured with the FO-SPR device. B) This diagram is further cut in individual reaction cycles.
Figure 6B:
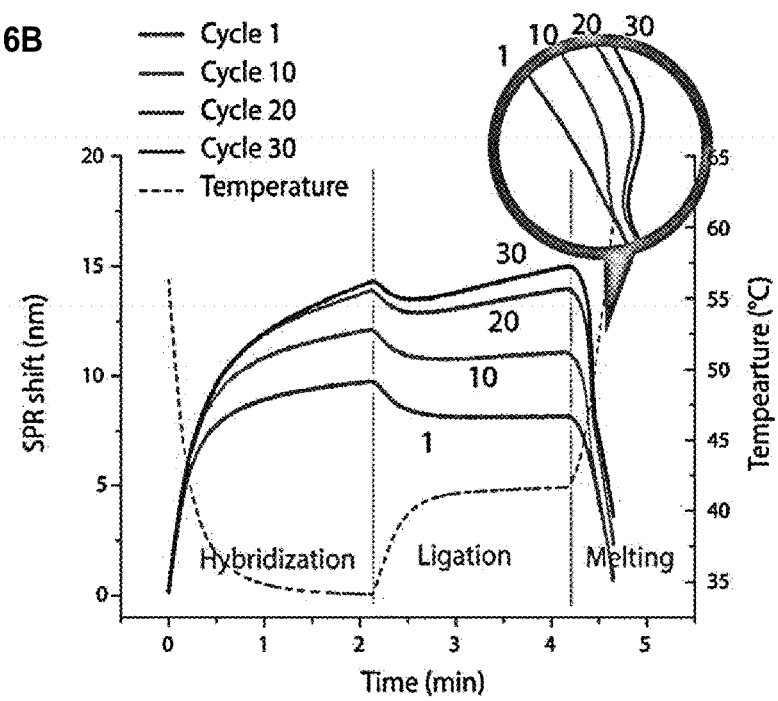

As described in FIG. 1, the FO-SPR LCR reaction consists of multiple ligation cycles, which are enabled by heating up and cooling down the reaction mixture. Because the heating of a fluid expands its volume, it also decreases the refractive index of the LCR reaction mixture, resulting in the SPR signal that is the exact inverse of the temperature signal (FIG. 6). This temperature effect is clearly visible in the FO-SPR signals on both measurement channels and allows easy processing of the data, as the refractive index changes can be used to determine the reaction cycle boundaries. Each reaction cycle is split in 3 phases, namely the hybridization phase where the DNA target strands can hybridize with the ligation probes, the ligation phase where the ligation enzyme covalently links perfectly hybridized probes and finally the melting phase where ligated products are melted from the target liberating it for the next round of ligation. The essential part of the LCR DNA amplification is the reverse ligation probe set as the exponential amplification and thus a high detection limit ($10^{-9}$ M of target DNA) are not attainable without them. During the hybridization step of each LCR cycle, the forward ligation products can hybridize to detection probes on the FO-SPR surface and Au NPs, forming a complex that is melted of in the melting phase of each reaction cycle.

Therefore, the acquired melting signal in the melting phase is uniquely attributable to the acquired LCR products and can thus be used to both identify and quantify the LCR product FIG. 7). Importantly, Au NP and FO-SPR probes cannot be ligated because they do not have a phosphate group necessary for the formation of a phosphodiester bond between the 3' hydroxyl group of probe 1 and the 5' phosphate group of probe 2.

Example 3: Quantification of DNA Targets Using the FO-SPR LCR Assay

Figure 8B:
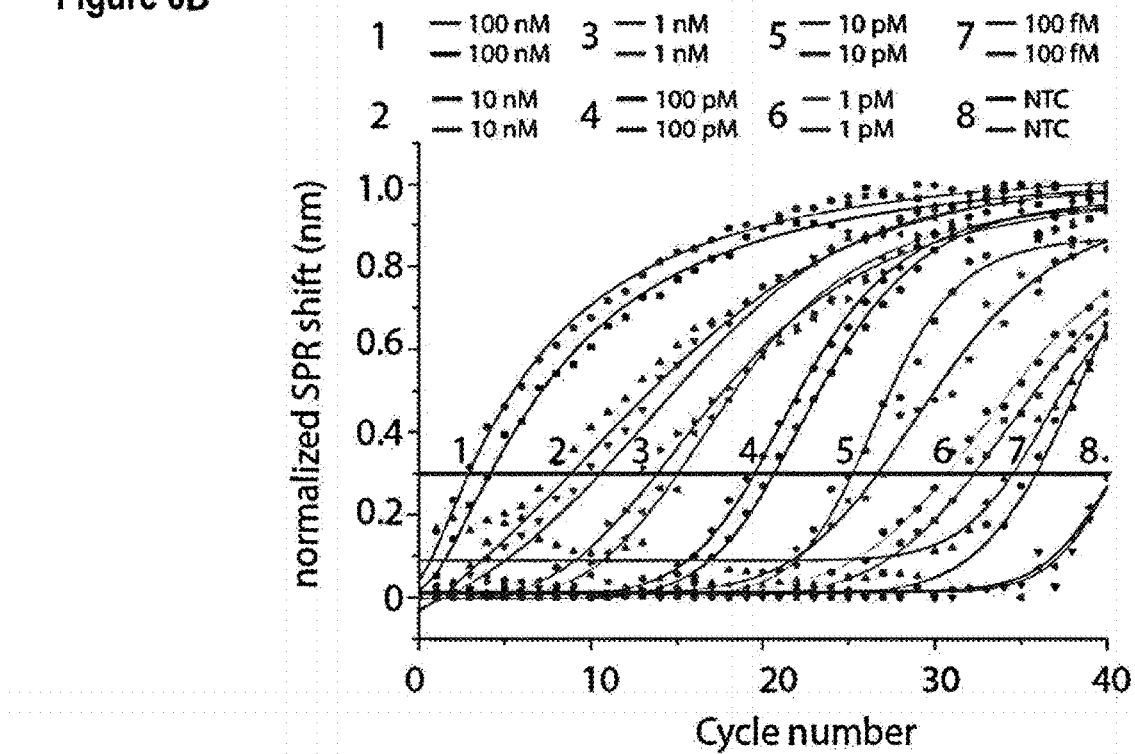
Figure 8C:
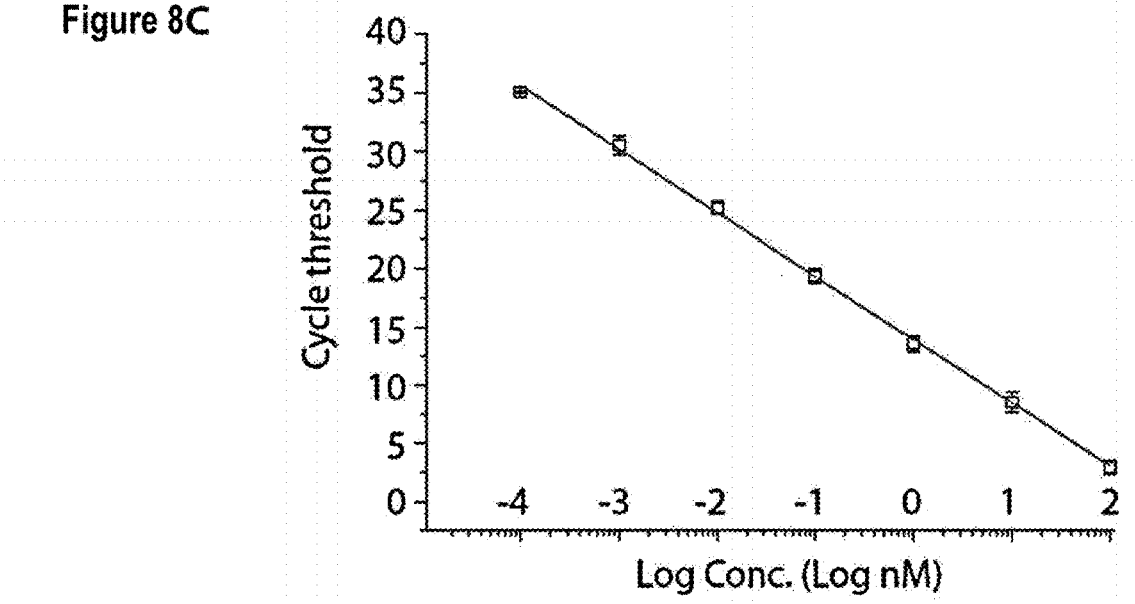

Next, the FO-SPR LCR assay was used to determine the target concentration by examining the number of LCR cycles necessary to obtain a FO-SPR melting point of the corresponding DNA target. In FIG. 8 part A, the concept is shown for a WT DNA target concentration of 100 fM. Out of 40 LCR cycles performed, no clear melting point was observed for this target in the first 27 cycles. In the subsequent cycles, a melting point appeared first at 51° C. followed by gradual increase towards 52.3° C. This shift in $T_m$ is expected and can be attributed to the dependence of $T_m$ on the increasing target concentration through LCR cycles [Gudnason et al. *Nucl. acids res.*, 2007, 35, e127]. In comparison with the $T_m$ obtained during the DNA melting optimization experiments described in paragraph 4.2, the $T_m$ has shifted almost 7° C., this is both a result from shorter hybridization times in the actual LCR assay and slight differences in ionic makeup of the reaction mixture in comparison with the pure buffer used during the optimization experiments.

Similar FO-SPR LCR reactions were then performed for 7 different target concentrations (100 nM, 10 nM, 1 nM, 100 pM, 10 pM, 1 pM and 100 fM) including a negative control without DNA target (no template control, NTC). For each concentration, the height of melting peaks were derived from all 40 LCR cycles and normalized to 1. These values, represented in FIG. 8, part B as a function of the total number of reaction cycles, pointed out that an increasing number of LCR reaction cycles is necessary for lower target concentrations. At approximately the $35^{th}$ cycle, a positive melting signal became evident also for the NTC, suggesting either contamination of the reaction mixture with target DNA or the occurrence of non-specific amplification in the LCR assay at these later cycles. Next the cycle threshold was chosen—this is the minimal SPR shift above baseline—that is indicative of successful LCR amplification. By using a cycle threshold of 0.25 (horizontal line in part B of FIG. 8), Ct values for each target concentration were derived and plotted as a function of the concentration, resulting in a calibration curve for the FO-SPR LCR assay (FIG. 8, part C). The assay had a linear range spanning 7 orders of magnitude, which is only 1 order less than a conventional qPCR assay. The lowest detectable concentration was 100 fM, at lower concentrations; the Ct was indistinguishable from the Non template control signal. Thus, the LCR reaction improved the detection limit with 4 orders of magnitude in comparison with results from previously reported FO-SPR melting assays [Knez et al., *Small*, 2012, 8, 868-872]. Although still far from the detection limit of Qper, a considerable improvement in detection limit is possible Meyer et al., *Nucl. acids res.*, 2008, 36, e5]. For instance, at this time the ligation was not performed at the optimal ligation temperature of the enzyme (45-90° C.) because of the low hybridization temperature (35° C.), resulting in less than optimal assay [Barany, *PCR methods appl.* 1991, 1, 5-16.]. Better probe design and selection of targets would allow the LCR assay to be performed at higher hybridization temperatures, which can improve ligase performance and eliminate non-specific binding, thus further decreasing the detection limit.

Example 4: Target Identification Using the FO-SPR LCR Assay

A final experiment was done to evaluate the performance of the FO-SPR LCR reaction for SNP detection. In order to detect a SNP within the target DNA strand using LCR assay, two new ligation probes, matching the SNP in the target, needed to be introduced in the assay. This adjustment was necessary to fulfill the requirement of the ligation enzyme for perfect sequence complementarity between target strand and two ligation probes. The FO-SPR assay allows discriminating the different LCR products because even a single base pair mismatch between the sensor immobilized hybridization probes and the ligated probes, will shift the $T_m$ to lower temperatures. Furthermore, mutations in the target sequence that will not affect the ligation reaction can also be discriminated with the FO-SPR assay. This means that not all mutations in the target sequence have to be known. The two LCR reactions performed both for WT and the MM target were compared with a melting analysis of the same targets (as described previously in Knez et al. cited above). Although the MM target clearly had a lower $T_m$ value compared to the WT, as expected, it surprisingly showed better yield of the LCR reaction FIG. 9. This can be explained by a difference in hybridization yield. The MM ligation probes are hybridized at a temperature further below the melting point of probes and targets, which is known to give a good hybridization yield [Rychlik et al., *Nucleic acids* res., 1990, 18, 6409-6412]. As for the WT ligation probes, the hybridization temperature are less optimal, explaining why there is a difference in ligation yield. Importantly, the $T_m$ measured during the LCR reaction allowed discrimination of the SNP bearing target from the WT target. In comparison with the melting analysis performed at a lower ramping speed, the melting signal obtained from the LCR assay was considerably lower with wider melting peaks. However, the resolution of the fast melting cycles was better with a $\Delta T_m$ between WT and MM target of 4.3° C. compared to 3.8° C. in the slow melting analysis. Similar trends in $T_m$ were also visible during the optimization experiments for thermal ramping speed. It can be speculated that the increased ramping speed results in the formation of less bonds between the Au NPs and the FO-SPR surface through the target DNA, which broadens the melting transition [Jin et al. cited above].

Example 5: Evaluation of Multiplex FO-SPR Performance

Simultaneous immobilization of different oligonucleotide probes on the FO-SPR sensor decreases the absolute number of each particular hybridization probe on the surface. Furthermore because the DNA sequence and length will influence immobilization efficiency, a particular hybridization probe can be favored during immobilization [Wolf et al. Langmuir: ACS j. surf coll. 2004, 20, 3357-3361]. To study this possible effect, an FO-SPR melting analysis was performed with FO-SPR sensors functionalized with individual and multiplex hybridization probes.

The melting analysis of the individual probe-target complexes was performed identically to the protocol optimized previously by Knez et al. cited above. A target concentration of 200 nM was used as this is well above the detection limit of the FO-SPR biosensor and should result in a clear signal. In FIG. 9A the results of the melting analysis are depicted. From this graph it can be observed that both bacterial targets can be easily identified, with the M. bovis and MAP target having a $T_m$ of 87° C. and 80° C., respectively. A similar experiment was successfully performed in the multiplex FO-SPR setting, with a mixture of both target sequences. (FIG. 9B).

However, these results reveal a small difference in the melting profile of the multiplex FO-SPR melt analysis in comparison with the individual melting assay. The melting signal, has a slightly lower peak with the $T_m$ being shifted to lower temperatures. This difference is most probably the result of the lower hybridization probe densities on the FO-SPR sensor and the Au NP surface. Similar trends of DNA melting assays are described in the literature when the densities of surface immobilized DNA probes are altered— [Jin et at cited above]. Nonetheless, the $\Delta T_m$ was only marginally different for individual and multiplex DNA melting analysis. The individual melting experiments resulted in a $\Delta T_m$ of 7.2 while for the multiplex experiments a window of 7.0° C. was obtained. It can be concluded from this experiment that the multiplex FO-SPR sensor can achieve a similar melting resolution as the singleplex FO-SPR melting analysis.

In a next experiment, the FO-SPR multiplex analysis was performed in a PCR master mix. Because the exact composition of this mixture is not known, an FO-SPR melting assay was performed to evaluate if a similar resolution could be obtained as in the previous experiment As can be seen from FIG. 10, two peaks, corresponding to each of both targets, could be resolved when using PCR master mix. Peak height was considerably lower than in the previous experiments, which can probably be attributed to a lower ionic strength. Also, the $\Delta T_m$ was reduced from 7.0° C. obtained in the previous experiments to 5.3° C. for multiplex FO-SPR analysis in the PCR master mix. These results show that buffer ionic strength has a strong influence on the resolution of the FO-SPR melting analysis. However, to prevent PCR enzyme inhibition, the ionic strength cannot be substantially altered.

Example 6. FO-SPR PCR Assay

In FIG. 11 nine cycles of a PCR reaction are shown. Initially, the FO-SPR signal is the inverse of the temperature change, which is continually monitored with a thermocouple. However, from the moment DNA target is amplified through PCR above the detection limit of the FO-SPR signal, the melting signal of the amplified DNA target will superimpose on the refraction index shift of the temperature measured with the FO-SPR sensor.

The effect of Au NP binding on the FO-SPR sensor through PCR products is clearly visible through the measurement of the individual cycles. In FIG. 13, all cycles of a standard multiplex PCR reaction for both targets at a concentration of 1 nM are presented. Here, it is clearer that the SPR signal is initially the inverse of the temperature, with a melting point becoming visible after few reaction cycles. The melting point of M. bovis becomes visible earlier due to the more efficient PCR. Once both PCR reactions have reached the detection limit of the sensor, two clear melting points are visible.

By taking the first order derivative of the SPR signal and temperature signal, the $T_m$ of each DNA target can be resolved very precisely, allowing an easy identification of both targets (FIG. 14). In comparison with the earlier optimization reactions, the $T_m$ of both targets is shifted approximately 3° C. The shift in $T_m$ is the result of a slightly higher ionic strength of buffer, necessary to stabilize the Au NPs in the PCR mixture. Use of increased ionic concentrations allowed keeping the Au NPs stable during the PCR reaction, as they appeared to be instable and prone to aggregation after extensive thermocycling (data not shown). The increased ionic strength was carefully optimized to prevent inhibition of the PCR reaction while having at the same time a stable Au NP solution capable of withstanding multiple thermal cycles.

Example 7. FO-SPR Mutation Analysis

The FO-SPR assay was tested for its sensitivity towards SNP mutations when present in the target sequences. For this experiment, the FO-SPR PCR assay was used to amplify and analyse 6 different DNA targets. First, the wild type MAP (*Mycobacterium avium* subspecies *paratuberculosis*) and *Mycobacterium bovis* targets were analysed at a concentration of 10 pM (versus 1 nM in the previous experiment). Both targets resulted in an almost identical $T_m$ values as in FIG. 14, suggesting that the technology is very robust.

Next, target sequences of MAP and *M. bovis* bearing a single mutation ($MM1_{MAP}$ and $MM1_{BOV}$) were analysed at the same concentrations of 10 pM. The mutation in the target sequence was located just outside the priming regions, in order to prevent PCR inhibition or loss of the mutation due to PCR amplification. The FO-SPR analysis of MM1 resulted in a clear melting signal with two melting points (FIG. 15).

The presence of a SNP in the M. bovis target changes $T_m$ value only for 0.5° C., while the change for MAP target $T_m$ is 1.3° C. This difference is the result of the target length. Thus, SNP will have a bigger influence on hybridization and consequently melting of a shorter target, i.e. MAP sequence that is 55 bp long compared to M. Bovis, which is 76 bp long.

To evaluate whether it is possible to differentiate targets with a single mutation from targets bearing multiple mutations, the FO-SPR PCR assay was applied to analyze both targets with three SNPs ($MM3_{MAP}$ and $MM3_{BOV}$). As can been seen from the results in FIG. 16, the extra mutations resulted in a larger change of the $T_m$ values for both targets compared to wild type sequences. The $\Delta T_m$ for the MAP target increased to 1.5° C. and for M. bovis to 1.0° C. Although these results need a further evaluation they give a first indication of the possibilities of the FO-SPR biosensor to discriminate between targets bearing single and multiple mutations.

Furthermore, it can be seen that both melting peak and cycle numbers are affected by the mutations present in the target sequences when the FO-SPR melting peak height is plotted versus the PCR cycle number for both WT and MM targets (FIG. 18). When this signal for the WT is compared with targets bearing either single or triple mutations, it is evident that more PCR cycles are needed for both mutated targets to reach the FO-SPR detection limit. Moreover, melting peaks are substantially smaller for both mutated targets in comparison with the melting signal of the WT target. Because mutations were not located in the priming regions and therefore could not influence PCR efficiency, these findings can only be explained by a lower hybridization efficiency of the two hybridization probes on FO-SPR sensor surface and Au NPs. The lower hybridization efficiency results from base pair mismatches between the target DNA with mutations and the immobilized hybridization probes on the FO-SPR biosensor and the gold nanoparticles. As a result the detection limit of the FO-SPR PCR biosensor for target sequences with mutations will always be slightly higher than for the wild type targets.

Materials & Methods
Reagents

The chemically synthesized oligonucleotides were purchased from integrated DNA technologies (Haasrode, Belgium) an overview can be found in Table 1. Both capture probes, used to capture the target sequence, are modified with a 3' C3 or 5' C6 thiol modifier (—SH) for immobilization of the oligonucleotides on the FO-SPR sensor and the Au NPs gold surfaces, respectively. All chemicals were purchased from Sigma-Aldrich (Bornem, Belgium) unless stated otherwise.

The below section provides sequences of probes and primers to perform the method of the present invention.

TABLE 1

Overview of oligonucleotides Bacillus anthracis detection

| OLIGONUCLEOTIDE | SEQ ID NO |
|---|---|
| Targets (5'→3') | |
| Wildtype (WT)<br>ATC CTT ATC AAT ATT TAA CAA TAA<br>TCC CTC | SEQ ID NO: 1 |
| Mismatch (M/M)<br>ATC CTT ATC AAT GTT TAA CAA TAA<br>TCC CTC | SEQ ID NO: 2 |
| Probes (5'→3') | |
| Ligation probe FW 1<br>/5Phos/AAT ATT GAT AAG GAT | SEQ ID NO: 3 |
| Ligation probe FW 2<br>GAG GGA TTA TTG TTA | SEQ ID NO: 4 |
| Ligation probe Rev 1<br>/5Phos/TAA CAA TAA TCC CTC | SEQ ID NO: 5 |
| Ligation probe Rev 2<br>ATC CTT ATC AAT ATT | SEQ ID NO: 6 |
| Ligation probe FW 2 Mismatch<br>/5Phos/AAC ATT GAT AAG GAT | SEQ ID NO: 7 |
| Ligation probe Rev 1 Mismatch<br>ATC CTT ATC AAT GTT | SEQ ID NO: 8 |
| Probe FO-SPR<br>TAA CAA TAA TCC CTC $A_{20}$/3ThioMC3-D/ | SEQ ID NO: 9 |
| Probe Au NP<br>/5ThioMC6-D/$A_{20}$ ATC CTT ATC AAT ATT | SEQ ID NO: 10 |

An overview of the targets, capture probes and primer sequences for detecting of Mycobacterium bovis and Mycobacterium avium subspecies paratuberculosis (MAP) and discriminating both species are shown in Table 2. Both capture probes, used to capture the target sequence, are modified with a 3' C3 or 5' C6 thiol modifier (—SH) for immobilization of the oligonucleotides on the FO-SPR sensor and the Au NPs gold surfaces, respectively. The free 3' end of the hybridization probes was blocked from extension by the polymerase enzyme using a 3' phosphate modification.

TABLE 2

Overview of used oligonucleotides

| OLIGONUCLEOTIDES | SEQ ID NO |
|---|---|
| Targets (5'→3') | |
| M. bovis Wild Type (WT), 76 bp<br>GCA GAA GCG CAA CAC TCT TGG AGT GGC CTA CAA CGG<br>CGCTCT CCG CGG CGC GGG CGT ACC GGA TAT CTT AGC<br>TGGT | SEQ ID NO: 11 |
| M. bovis 5' Mismatch 1 SNPs ($MM1_{BOV}$), 76 bp<br>GCA GAA GCG CAA CAC TCT TTG AGT GGC CTA CAA CGG<br>CGCTCT CCG CGG CGC GGG CGT ACC GGA TAT CTT AGC<br>TGG T | SEQ ID NO: 12 |

TABLE 2-continued

Overview of used oligonucleotides

| OLIGONUCLEOTIDES | SEQ ID NO |
|---|---|
| *M. bovis* 5' Mismatch 3 SNPs (MM3$_{BOV}$), 76 bp<br>GCA GAA GCG CAA CAC TCT TTG AGC GTC CTA CAA CGG<br>CGCTCT CCG CGG CGC GGG CGT ACC GGATAT CTT AGC<br>TGG T | SEQ ID NO: 13 |
| MAP Wild Type (WT), 56 bp<br>TGG TCG TCT GCT GGGTTG ATC TGG ACA ATG ACG GTT<br>ACG GAG GTG GTT GTG GC-3 | SEQ ID NO: 14 |
| MAP 5' Mismatch 1 SNPs (MM1$_{MAP}$), 56 bp<br>TGG TCG TCT GCT GGG TTG ATA TGG ACA ATG ACG GTT<br>ACG GAG GTG GTT GTG GC-3 | SEQ ID NO: 15 |
| MAP 5' Mismatch 3 SNPs (MM3$_{MAP}$), 56 bp<br>TGG TCG TCT GCT GGG TTG ATA TTA ACA ATG ACG GTT<br>ACG GAG GTG GTT GTG GC | SEQ ID NO: 16 |
| Primers (5'→3') | |
| *M. bovis* primer forward, 19 bp<br>GCA GAA GCG CAA CAC TCT T | SEQ ID NO: 17 |
| *M. bovis* primer reverse, 22 bp<br>ACC AGC TAA GAT ATC CGG TAC G | SEQ ID NO: 18 |
| MAP primer forward, 19 bp<br>TGG TCG TCT GCT GGG TTG A | SEQ ID NO: 19 |
| MAP primer reverse, 20 bp<br>GCC ACA ACC ACC TCC GTA AC | SEQ ID NO: 20 |
| Hybridization probes (5'→3') | |
| *M. bovis* probe 1, 48 bp<br>CGC CGT TGT AGG CCA CTC CAA GAG TGT TGC GCT TCT<br>GCT TTT TTT TTT-SH | SEQ ID NO: 21 |
| *M. bovis* probe 2, 48 bp<br>SH-TTT TTT TTT TAC CAG CTA AGA TAT CCG GTA CGC<br>CCG CGC GCG GGA GAG-Phos | SEQ ID NO: 22 |
| MAP probe 1, 45 bp<br>TGT CCA GAT CAA CCC AGC AGA CGA CCATTT TTT TTT<br>TTT TTT TTT-SH | SEQ ID NO: 23 |
| MAP probe 2, 44 bp<br>SH-TTT TTT TTT TTT TTT TTT GCC ACA ACC ACCTCC GTA<br>ACC GTC AT-Phos | SEQ ID NO: 24 |

Thiol-functionalized DNA was immobilized on the Au NPs by adding 1 µM of 5' thiol functionalized DNA oligo activated with dithiothreitol (DTT, 0.1 M in PB 0.18 mM, pH 8.3) to break up thiol dimers that could inhibit the DNA functionalization. DNA was first purified using a sephadex column (GE, Oslo, Norway) to remove any traces of active DTT before it was added to the concentrated nanoparticle solution. A fast salt maturation protocol was used to maximize the DNA loading on the Au NPs [Hurst et al., *Anal. Chem.*, 2006, 78, 8313-8318]. Afterwards, Au NPs were washed three times in phosphate buffer with 0.01% SDS and stored at 4° C. prior to use.

TABLE 3

| primers and probes for the detection of celery | |
|---|---|
| Mtd3 target:<br>CCCGTACGAGATATATTTTTGTCTGGTTTGAGATATATAT<br>TACATGCTGAGTCACGATGAGCGTGTACTGAGTCAGTGT<br>TATGTTTGGATTACGGTGTGATGAGTCAGC | SEQ ID NO: 25 |
| Mtd3 forward: CCCGTACGAGATATATTTTTGTCTGG | SEQ ID NO: 26 |
| Mtd3 reverse: GCTGACTCATCACACCGTAATCC | SEQ ID NO: 27 |

TABLE 3-continued primers and probes for the detection of celery

Hybridization probe on sensor fibre:                SEQ ID NO: 28
GTG ACT CAG CAT GTA ATA TAT ATC TCA AAC CAG
ACA AAA ATA TAT CTC GTA CGG GTT TTT TTT
TT/3ThioMC3-D/

Hybridization probe on metal beads:                 SEQ ID NO: 29
/5ThioMC6-D/TTT TTT TTT TGC TGA CTC ATC ACA CCG
TAA TCC AAA CAT AAC ACT GAC TCA GTA CAC GCT
CAT C/3Phos/

Celery (*Apium graveolens*) is one of the many food ingredients which can cause food allergy. The above primers allow to determine in a qualitative and quantitative the presence of DNA of the mannitol dehydrogenase gene of cellery.

Such a kit can be expanded with further primers or probes of other allergens to provide a multiplex assay to determine presence and amount of allergens in food samples.

FO-SPR Sensor Fabrication and Au NP Functionalization

Figure 3:
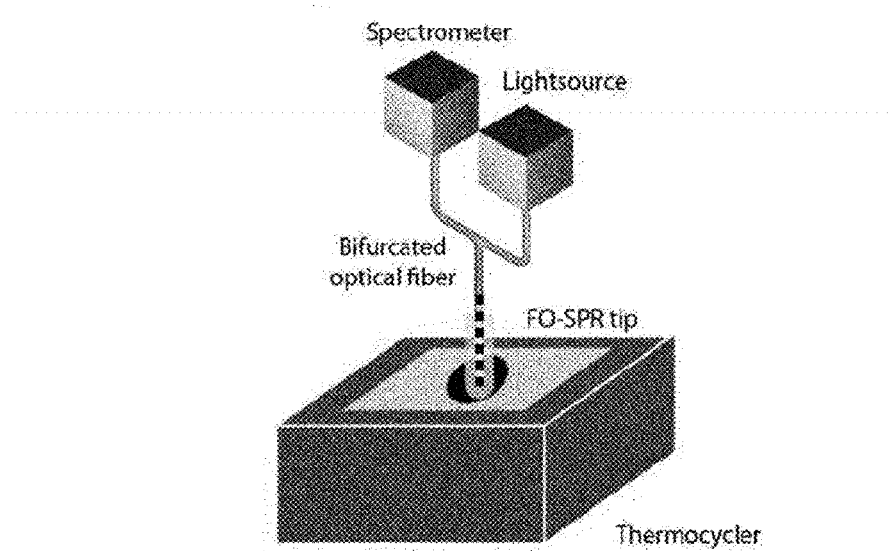
FIG. 3 shows schematic close up of the sensing device with a light source for incident light, which excites surface plasmons, and a spectrometer which analyses reflected light in the SPR sensor tip.

The FO-SPR device and sensors were manufactured as described previously [Pollet et al., *Biosens. Bioelectr.*, 2009, 25, 864-869]. In short, the fibre optic (FO) sensor device consists of a white light source, a miniature UV-VIS spectrophotometer and a FO sensor. The FO Surface Plasmon Resonance (SPR) setup enables replaceable and interchangeable FO-SPR sensors to be coupled with a bifurcated optical fibre to guide white light from the light source into the sensor. The light will first pass the SPR sensitive gold zone, afterwards it will reflect back at the tip and travel towards the spectrometer (FIG. 3). The SPR sensitive zones comprises a thin gold layer on the fibre optic silica core where the light is coupled to the valence electrons of the gold layer and a propagating surface plasmon wave is generated. This coupling of light results in a wavelength dependent reduced intensity (dip) in the reflected light that is captured with the spectrometer. Binding phenomena at the gold surface changing the local refractive index will result in a shift of the typical spectral resonance SPR-dip recorded by the spectrometer. When the gold layer is coated with DNA as is the case in the FO-SPR high resolution melting (HRM) assay, the FO-SPR sensor can be used to monitor interactions of this immobilized DNA with free DNA in a solution. In order to augment assay sensitivity the complementary gene probes are labelled with Au nanoparticles (NP).

The setup was extended with a thermocycler to control the sample temperature and a robotic arm to automate fibre optic probe handling. The thermocycler temperature was monitored externally with three highly responsive T-type thermocouple threads. This allowed us to monitor the exact temperature at the FO surface and derive the exact melting temperature by combining temperature data with the SPR sensorgram. Spectrometer data was processed in real-time using spectrometer driver software and an in house written script. Temperature logging was also managed in the in house written custom program.

FO sensors were designed and manually manufactured as previously described in Pollet et al., *Biosens. Bioelectr.*, 2009, 25, 864-869. In short, a 400 µm 0.39 NA multimode TEQS optical fibre was cut consistent to a length of 5 cm, next the fibre was assembled into an SMA connector after removal of the protective cladding. Following, the fibre end was placed in acetone for 5 min to loosen the hard polymer cladding. Afterward, the FO sensor was carefully cleaned with Isopropyl ethanol and rinsed with water. Subsequently, the FO sensors were coated with a 50 nm gold layer using a sputter coater. The freshly coated FO sensors were immediately incubated with 1 µM reduced DNA with a 3' thiol end-group (Table 1&2) to create a dense DNA surface coating. The reduction of the thiol-DNA was done by incubating 50 µM thiol-DNA for 3 h in 0.1 M phosphate buffer (PB) containing 0.18 M Dithiotreithol. Afterwards, the DTT was removed from the activated DNA using NAP5 Sephadex columns. The FO sensors were incubated overnight in the DNA PB solution to get a dense DNA covering. Afterwards the FO sensor was rinsed three times in PB with 0.01% SDS and stored in a fridge. The final DNA density on the FO sensor was estimated $0.40 \pm 0.02$ strands per $nm^2$.

Figure 2:
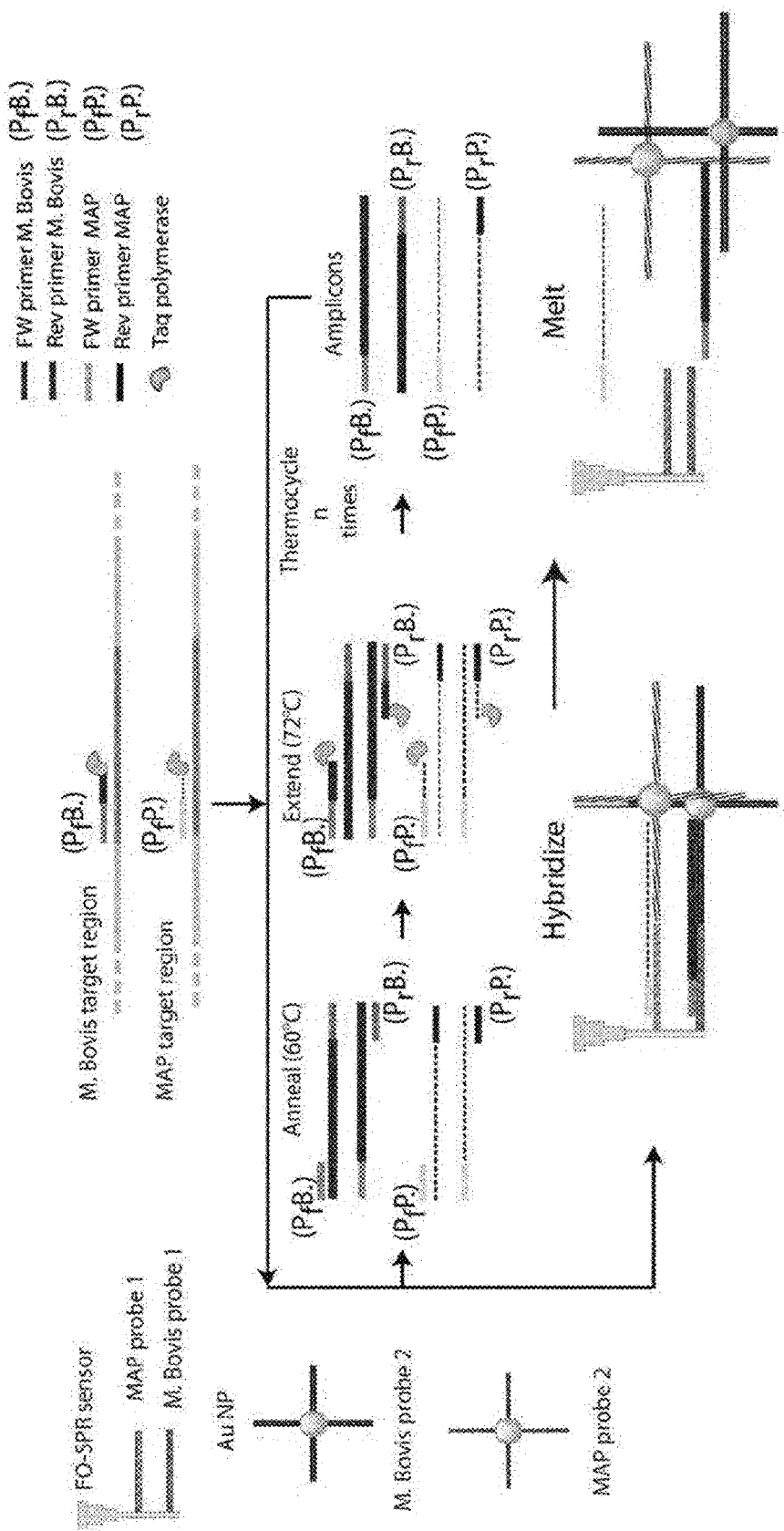
FIG. 2 is a conceptual overview of FO-SPR quantitative multiplex PCR, the components used for FO-SPR are visualized on the left while all PCR components are visualized in the top right corner. The PCR primers specific for MAP (*Mycobacterium avium* subspecies *paratuberculosis*) and *Mycobacterium bovis* will be used to amplify a target region during a standard PCR reaction. The amplicons of both MAP and *M. bovis* will be able to hybridize during the PCR reaction to complementary probes on the FO-SPR sensor and those on Au NPs. During the normal thermocycling used to denature the PCR amplicons for the PCR reaction, the FO-SPR sensor can register the Tm of the PCR amplicons and as a result perform n melting analyses, which can be used to identify different targets.

Citrate stabilized Au NPs, with a mean diameter of 20 nm, were purchased from BBI international (Cardiff, United Kingdom) and functionalized using the protocol described previously by Knez et al. cited above. This standard protocol was adjusted for the simultaneous immobilization of two hybridization probes during the functionalization process. Both probes were added to the Au NPs in equal amounts (FIG. 2).

Gold Surface Backfilling

Both the FO-SPR sensor and Au NPs were backfilled, prior to use in the LCR assay. Backfilling is a process used to fill in 'empty spots' in between DNA molecules immobilized on a surface, which is often done using alkane thiols with a PEG moiety [Lee et al., *Anal. Chem.*, 2006, 78, 3316-3325]. Here, backfilling is performed in order to make the DNA functionalized gold surfaces more stable at elevated temperatures as well as protein repellant, preventing enzyme inhibition during the LCR reaction [Stakenborg et al., *Nanopart Res*, 2008, 10, 143-152; Janssen et al., *Nanotech.*, 2012, 23, 235503]. Both FO-SPR sensors and Au NPs were incubated for 3 h with a 50 µM alkane thiol PEG (Polypure, Oslo, Norway) dissolved in pure ethanol. Afterwards, the FO-SPR sensor surface and Au NPs were washed 3 times with a 0.01% SDS phosphate buffer.

DNA Melting Analysis

The multiplex DNA melting analysis on the FO-SPR device was performed using a hybridization step at 55° C. for 10 minutes, followed by an increase in temperature to 90° C. at 0.1° C./s. Experiments were performed in a 10 mM Tris HCl buffer with 2.5 mM $MgCl_2$ and 60 mM NaCl and 0.1% triton X-100. The target DNA concentration was 500 nM when individual DNA targets were analyzed and 250 nM when a multiplex target analysis was carried out.

Ligation Chain Reaction

The LCR was performed to link the 5' phosphate-functionalized probe 2 to the 3' end of probe 1. A thermophilic ligation enzyme (9° N™ DNA Ligase, New England Bioscience, Ipswich, USA) was used as it can withstand thermocycling of the reaction solution between different temperatures: the probe hybridization temperature (2 min at 35° C.), the optimal ligation temperature (2 min at 42.5° C.) and the denaturing temperature of the ligation product (5 s at 70° C.). The thermal ramping speed had to be lowered compared to 5° C./s standardly used in LCR assays to allow a good FO-SPR signal acquisition during DNA melting. It was optimized for achieving reasonable speed and thus safeguarding the total assay time (1° C./s). Another parameter that was optimized was the ligation buffer, which standardly contains DTT, known to reduce thiol bonds [Kuwajima et al., Biochem., 1990, 29, 8240-8249.].

The final ligation reaction mixture used for the FO-SPR LCR calibration curves and sample analysis consisted of 10 µL ligase buffer (10× concentrated), 10 µL of 9° N enzyme (10 u/µL), 2.5 µL Fw ligation probes (10 µM, for each target sequence), 2.5 µL Rev ligation probes (1 µM, for each target sequence), 50 µL Au NPs (0.5 nmol/L in distilled nuclease free $H_2O$), 10 µL target DNA, 15 µL distilled nuclease free $H_2O$ making a total reaction volume of 100 µL. After adding all these components the LCR reaction mixture was mixed very carefully and covered with 60 µL mineral oil (Immobiline DryStrip Cover Fluid, GE healthcare, Diegem, Belgium) to prevent evaporation during thermocycling.

Polymerase Chain Reaction (PCR)

PCR was performed to extend primers for a specific region of *M. bovis* and MAP. Primers for MAP were adopted from Ravva & Stanker, *J. microbiol. l methods,* 2005, 63, 305-317, who selected these primers using the insertion sequence IS900, a repetitive element present only in the MAP genome. Primers for *M. bovis* were designed for the so-called regions of difference (RD), which contain sequence deletions in the genome of *M. bovis* that are not present in other Mycobacteriacae.

A PCR mastermix (DimerEraser, Takara, Shiga, Japan) containing all necessary components for the PCR reaction, except primers, was used. The total reaction volume was 100 µL, this volume is considerably larger than for a standard PCR reaction, to submerge the FO-SPR sensor completely in the PCR mixture. The reaction mixture consisted of 50 µL Takara mastermix, 3 µL of each primer (300 nM final concentration), 20 µL Au NPs (1.0 nmol/L in distilled nuclease free $H_2O$), 4 µL $MgCl_2$ (50 mM), 4 µL NaCl, 10 µL target DNA. The reaction mixture was protected from evaporation during thermocycling by covering it with a layer of mineral oil (Immobiline DryStrip Cover Fluid, GE healthcare, Diegem, Belgium).

The sample temperature was cycled according to the following program:
Enzyme activation
30 sec at 95° C.
Three step PCR protocol (45 consecutive cycles):
30 sec at 55° C. (ramp speed=5.0° C./s)
30 sec at 72° C. (ramp speed=5.0° C./s)
5 seconds 90° C. (ramp speed=1.0° C./s)
Data Processing Data acquisition on the two spectrometers and NiDaq coupled thermocouples was done with the in-house developed LabView program (National Instruments, Austin, Tex.) as described previously in Knez et al. cited above. Once the SPR data and thermocouple data were combined, a first order derivative was made for each LCR melting cycle. The resulting melting peak was fitted using a Gaussian fit in Matlab (the mathworks, Natick, USA) to determine the melting temperature ($T_m$) and evaluate the melting peak quality for each LCR cycle.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

---

The invention claimed is:

1. A method for real-time detection of a target nucleic acid in a sample, comprising the steps of:
   a) providing a reaction chamber comprising
      a mass-sensitive sensor, wherein the sensor is functionalized with a first nucleic acid probe that hybridizes to said target nucleic acid, and
      metal nanoparticles functionalized with a second nucleic acid probe that hybridizes to said target nucleic acid, wherein said first and second probes bind to different regions of said target nucleic acid such that the first and second probes can hybridize simultaneously to said target nucleic acid,
   b) adding a sample to the reaction chamber and performing, with the sensor being present within the reaction chamber, a nucleic acid amplification of the target nucleic acid using non-immobilized, non-metal functionalized probes complementary to the target nucleic acid, wherein during the annealing step of the amplification method, amplified target nucleic acid forms a complex with the first probe on the sensor and the second probe with the metal nanoparticles, and
   c) determining during a denaturation step of the nucleic acid amplification reaction, the presence of the target nucleic acid at the sensor by measuring at the melting temperature of the complex formed in step b, the release of the amplified target nucleic acid from the sensor.

2. The method according to claim 1, which is a multiplex assay for the detection of a plurality of different target nucleic acids, wherein for each of the different target nucleic acids, a specific set of a first nucleic acid probe on the sensor that hybridizes to a target nucleic acid and a second nucleic acid probe on the metal nanoparticles are provided, and wherein non-immobilized, non-metal functionalized amplification probes are provided to amplify all target nucleic acids, such that for each of the complexes of a different nucleic acid target and its corresponding first and second nucleic acid probe a different melting temperature is obtained, and wherein by measuring at the melting temperature of each of the different nucleic acid target complexes, the presence of each of the different target nucleic acids on the sensor is determined.

3. The method according to claim 2, wherein the difference in melting temperature between each of the different complexes is at least 0.3° C.

4. The method according to claim 2, wherein said first probes for the different target nucleic acids are immobilized on the same sensor surface.

5. The method according to claim 2, wherein the difference in melting temperature between each of the different complexes is at least 1.5° C.

6. The method according to claim 1, wherein said non-immobilized, non-metal functionalized probes for amplification are present in the reaction chamber prior to the addition of the sample.

7. The method according to claim 1, wherein said metal nanoparticles are gold nanoparticles.

8. The method according to claim 1, wherein said nucleic acid amplification is a Polymerase Chain Reaction.

9. The method according to claim 1, wherein said nucleic acid amplification is a Ligation Chain Reaction (LCR).

10. The method according to claim 1, comprising comparing each amplification cycle with a reference curve indicating nucleic acid concentration as a function of amplification cycles.

11. The method according to claim 10, wherein said amplification cycles comprise at least one cycle in which melting rates are in a range between 0.1° C./s-1.5° C./s.

12. The method according to claim 10, wherein the denaturation step of said amplification cycles is less than 5 seconds in duration.

13. The method according to claim 1, wherein said mass-sensitive sensor is an optic sensor.

14. The method according to claim 13, wherein said optic sensor is a fibre optic sensor.

15. The method according to claim 14, wherein a refractive index at said fibre optic sensor is continuously measured during the amplification cycles of the nucleic acid amplification reaction.

16. The method according to claim 13, wherein the melting temperature is determined by shifts in refractive index at specific temperatures.

17. The method according to claim 16, comprising comparing the measurable shifts in the refractive index signals with a calibration curve indicating expected melting temperatures for each target nucleic acid.

18. The method according to claim 16, wherein quantities of target nucleic acid are determined in real-time by counting amplification cycles needed to produce the measurable shift in refractive index.

* * * * *